US008500727B2

(12) United States Patent  (10) Patent No.: US 8,500,727 B2
Aramayo  (45) Date of Patent: Aug. 6, 2013

(54) METHODS, SYSTEMS, AND DEVICES FOR PERFORMING ELECTROSURGICAL PROCEDURES

(75) Inventor: Thomas F. Aramayo, Draper, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 397 days.

(21) Appl. No.: 12/464,591

(22) Filed: May 12, 2009

(65) Prior Publication Data

US 2010/0030212 A1 Feb. 4, 2010

Related U.S. Application Data

(60) Provisional application No. 61/052,733, filed on May 13, 2008.

(51) Int. Cl.
*A61B 18/14* (2006.01)
(52) U.S. Cl.
USPC .............................. 606/34; 606/45
(58) Field of Classification Search
USPC ................... 606/32–34, 41, 45–50
See application file for complete search history.

(56) References Cited

U.S. PATENT DOCUMENTS

| | | | |
|---|---|---|---|
| 2,917,614 A | 12/1959 | Caliri et al. | |
| 4,202,337 A | 5/1980 | Hren et al. | |
| 4,228,800 A | 10/1980 | Degler, Jr. et al. | |
| 4,658,819 A | 4/1987 | Harris et al. | |
| 4,850,353 A | 7/1989 | Stasz et al. | |
| 5,013,312 A | 5/1991 | Parins et al. | |
| 5,122,137 A * | 6/1992 | Lennox ........................ 606/40 |
| 5,423,810 A | 6/1995 | Goble et al. | |
| 5,514,129 A | 5/1996 | Smith | |
| 5,558,671 A | 9/1996 | Yates | |
| 5,599,344 A | 2/1997 | Paterson | |
| 5,628,745 A | 5/1997 | Bek | |
| 5,817,093 A | 10/1998 | Williamson, IV et al. | |
| 5,976,128 A | 11/1999 | Schilling et al. | |
| 6,039,735 A | 3/2000 | Greep | |
| 6,056,747 A | 5/2000 | Saadat et al. | |
| 6,066,137 A * | 5/2000 | Greep ............................ 606/45 |
| 6,228,080 B1 | 5/2001 | Gines | |
| 6,238,387 B1 | 5/2001 | Miller, III | |
| 6,348,051 B1 | 2/2002 | Farin et al. | |
| 6,398,779 B1 * | 6/2002 | Buysse et al. .................... 606/34 |
| 6,447,509 B1 | 9/2002 | Bonnet et al. | |
| 6,511,479 B2 | 1/2003 | Gentelia et al. | |
| 6,533,781 B2 | 3/2003 | Heim et al. | |
| 6,589,239 B2 | 7/2003 | Khandkar et al. | |
| 6,620,157 B1 | 9/2003 | Dabney et al. | |
| 6,673,072 B1 | 1/2004 | Garito et al. | |
| 6,692,489 B1 | 2/2004 | Heim et al. | |
| 6,740,079 B1 | 5/2004 | Eggers et al. | |
| 6,843,789 B2 | 1/2005 | Goble | |
| 6,855,142 B2 | 2/2005 | Harano et al. | |
| 6,890,331 B2 | 5/2005 | Kristensen | |

(Continued)

*Primary Examiner* — Michael Peffley
(74) *Attorney, Agent, or Firm* — Workman Nydegger

(57) ABSTRACT

An electrosurgical system including a sharpened electrosurgical electrode, which can have a coated surface, and an automatically adjusting electrosurgical wave generator is disclosed. The automatically adjusting wave generator and the sharpened electrode tip provide or enhance the properties, attributes and/or characteristics of the electrosurgical system and prevent tissue damage and reduce incidences of post-operative complications, thereby quickening the healing process. The wave generator detects various circuit parameters and automatically adjusts the output settings, such as the output power level, based on the various circuit parameters, such as tissue impedance, to prevent undesirable tissue damage.

20 Claims, 20 Drawing Sheets

U.S. PATENT DOCUMENTS

| | | |
|---|---|---|
| 6,893,435 B2 | 5/2005 | Goble |
| 6,923,804 B2 | 8/2005 | Eggers et al. |
| 6,974,452 B1 | 12/2005 | Gille et al. |
| 7,044,948 B2 | 5/2006 | Keppel |
| 7,060,063 B2 * | 6/2006 | Marion et al. .................. 606/34 |
| 7,066,936 B2 | 6/2006 | Ryan |
| 7,094,233 B2 | 8/2006 | Desinger |
| 7,137,980 B2 * | 11/2006 | Buysse et al. .................. 606/34 |
| 7,150,748 B2 | 12/2006 | Ebbutt et al. |
| 7,255,694 B2 | 8/2007 | Keppel |
| 7,300,435 B2 | 11/2007 | Wham et al. |
| 7,367,973 B2 | 5/2008 | Manzo et al. |
| 7,377,919 B2 | 5/2008 | Heim et al. |
| 2007/0005059 A1 | 1/2007 | Heim et al. |
| 2007/0005060 A1 | 1/2007 | Heim et al. |
| 2007/0093800 A1 * | 4/2007 | Wham et al. .................. 606/34 |
| 2007/0156137 A1 | 7/2007 | Geisel |
| 2007/0173805 A1 * | 7/2007 | Weinberg et al. ............... 606/34 |
| 2008/0103494 A1 | 5/2008 | Rioux et al. |
| 2008/0119841 A1 | 5/2008 | Geisel |
| 2008/0249526 A1 | 10/2008 | Knowlton |

* cited by examiner

METHODS, SYSTEMS, AND DEVICES FOR PERFORMING ELECTROSURGICAL PROCEDURES

CROSS-REFERENCE TO RELATED APPLICATIONS

This application claims priority to and the benefit of U.S. Provisional Patent Application Ser. No. 61/052,733, filed May 13, 2008, entitled "Methods, Systems, and Devices for Performing Electrosurgical Procedures," the disclosure of which is incorporated herein by this reference.

BACKGROUND OF THE INVENTION

1. The Field of the Invention

The present invention relates generally to electrosurgical systems. More specifically, the present invention relates to using a combination of a sharpened electrosurgical electrode with a customized power curve to enhance the cutting efficiency of the electrode, reduce unwanted tissue damage, and facilitate improved post-operative healing.

2. The Relevant Technology

In the area of electrosurgery, medical procedures of cutting tissue and/or cauterizing leaking blood vessels are performed by utilizing radio frequency (RF) electrical energy. The RF energy is produced by a wave generator and transmitted to a patient's tissue through a hand-held electrode that is operated by a surgeon. The hand-held electrode delivers an electrical discharge to cellular matter of the patient's body adjacent to the electrode. The discharge causes the cellular matter to heat up in order to cut tissue and/or cauterize blood vessels.

The high temperatures involved in electrosurgery can cause thermal necrosis of the tissue adjacent the electrode. The longer tissue is exposed to the high temperatures involved with electrosurgery, the more likely it is that the tissue will suffer thermal necrosis. Thermal necrosis of the tissue can decrease the speed of cutting the tissue and increase post-operative complications, eschar production, and healing time, as well as increasing incidences of heat damage to tissue away from the cutting site.

As noted above, RF energy is produced by a wave generator and transmitted to a patient's body adjacent to the electrode during electrosurgery. The concentration of the RF energy discharge affects both the efficiency with which the electrode is able to cut tissue and the likelihood of tissue damage away from the cutting site. With a standard electrode geometry, the RF energy tends to be uniformly distributed over a relatively large area adjacent to the intended incision site. The generally uniform distribution of the RF energy discharge increases the likelihood of extraneous charge loss into surrounding tissue, which increases the likelihood of unwanted tissue damage in the surrounding tissue.

Additionally, typical electrosurgical wave generators requires the surgeon or other operating room personnel to adjust various output parameters of the wave generator, such as the power level and/or the frequency of the electrical discharge to be delivered to the patient's tissue. Properly adjusting these various settings requires great knowledge, skill, and attention from the surgeon or other personnel. Once the surgeon has made the desired adjustments to the various settings on the generator, the generator maintains those output parameters during electrosurgery. For example, if the surgeon were to set the output power level of the generator to 50 W and then touch the electrode to the patient to perform electrosurgery, the power level of the generator would quickly rise to and be maintained at 50 W. While setting the power level to a specific setting, such as 50 W, will allow the surgeon to cut through the patient's tissue, maintaining such a high power level increases the likelihood of thermal necrosis of the patient's tissue.

Therefore, it would be an advantage to have a wave generator that could provide sufficient power to effectively perform electrosurgery and an electrode that increases the concentration of the RF energy discharge, while at the same time limiting unwanted tissue damage, reducing post-operative complications, and facilitating quicker healing. The subject matter claimed herein, however, is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

The present invention relates to the combination of an electrosurgical electrode having a sharpened working edge and a relatively limited mass or thickness, and a customized power curve generated by a wave generator that is specifically tailored to work with the sharpened electrosurgical blade. More specifically, the present invention relates to the combination of an electrosurgical electrode having a sharpened working edge, a limited mass or thickness, and a customized power curve generated by an electrosurgical wave generator. The generator is adapted to sense the tissue impedance of a patient substantially in real-time and automatically adjust the generator's output power level in response to the tissue's impedance level. The automatic adjustment of the output power level in response to the changing tissue impedance enhances the results of the electrosurgery procedure. The enhanced results include reducing the difficulty of performing procedures, minimizing thermal necrosis and post-operative complications typically associated with electrosurgery, improving the quality and speed of post-operative healing, as well as providing self-regulating characteristics that both enhance the performance of the active electrode and contribute to the reduction in thermal necrosis.

Implementation of an exemplary embodiment of the present invention takes place in association with a surface, such as at least a portion of the surface of an electrosurgical electrode tip (also referred to herein as an electrode blade or blade) that may be used to cut tissue and/or cauterize blood vessels of a patient during an electrosurgical operation that includes the use of an electrosurgical wave generator that automatically adapts the output power level of the generator to a predetermined level based on the impedance level of the circuit.

An exemplary embodiment of the present invention provides an electrosurgical electrode having a working surface that is shaped or sharpened. Shaping the geometrical surface (s) to be used to effect electrosurgical cutting achieves an important concentration of electrosurgical energy to permit more rapid and effective cutting of tissue. Additionally, because cutting is effectuated as a result of the concentration of electrosurgical energy, rather than the sharpness of a normal mechanical scalpel, an electrode according to the present invention is safer to handle than a scalpel because the working surface of the electrode tip is not required to be as sharp as a scalpel, thus reducing the risk of a mechanical cut to a physician or other operating room personnel while handling the electrode. The concentration of electric field and energy transfer (as described below) due to the sharpened working edge of the electrode tip provides a marked improvement in charge concentration and tissue severance and results in reduced thermal necrosis, more rapid cutting, and reduced eschar production.

An exemplary embodiment of the present invention also provides an electrosurgical electrode tip that has a limited overall thickness and/or mass. Limiting the thickness and/or mass of the electrode tip limits the amount of latent heat that the electrode tip is able to retain. The latent heat that can build up in an electrode tip during an electrosurgical procedure can be transferred to the tissue around to the electrode tip. This transfer of thermal energy can cause undesirable necrotic damage in the tissue surrounding the incision site and not just at the incision site. Thus, reducing the thickness and/or mass of the electrode tip also reduces the amount of latent heat that the electrode tip can transfer to the surrounding tissue, thereby reducing the amount of undesirable tissue damage surrounding the incision site.

Exemplary embodiments of the present invention provide a sharpened and coated electrosurgical electrode tip. The electrosurgical electrode tip coating can comprise a non-stick coating, such as polytetrafluoroethylene ("PTFE") or TEFLON®, or a hybrid material that can include a combination of at least one of an organic material and an inorganic material to provide various desirable properties to the electrode, such as high temperature stability, flexibility, and a low temperature application.

Furthermore, an exemplary embodiment of the present invention provides an electrosurgical wave generator that can be used in combination with the sharpened, limited mass electrosurgical electrode tip to minimize tissue damage. The electrosurgical wave generator can include components for generating an electrical wave that can be used to effectuate electrosurgery. The electrosurgical wave generator can also include sensors for detecting various parameters of the electrosurgical circuit, such as the voltage, the current flowing through the circuit, and the impedance of a patient's tissue, for example. Additionally, the electrosurgical wave generator can be equipped with a processor that can be programmed to automatically change, at a relatively high speed/sampling rate, various output parameters of the wave generator based on the detected circuit parameters. For example, the wave generator can be programmed to maintain a specific output power level so long as the tissue impedance detected by the wave generator remains within a predetermined range. If the tissue impedance falls outside the predetermined range, the wave generator can automatically reduce the output power level to prevent undesirable tissue damage. Once the tissue impedance returns to within the predetermined range, the wave generator can automatically increase the output power level to enable the electrode tip to continue cutting the tissue.

The combination of a sharpened, low mass electrode tip and a customized power curve according to the present invention produces a self-limiting and self-regulating electrosurgical system. For instance, one embodiment of the electrosurgical system regulates the amount of power supplied to the electrode tip based upon the impedance between the electrode tip and the tissue that is contacting the electrode tip. Thus, as the impedance changes, whether due to changes in the temperature of the tissue or the amount of contact area between the electrode tip and the tissue, the power supplied to the electrode tip is automatically adjusted to account for these changes. Similarly, the electrosurgical system can regulate the output power based upon changes that result from changing surgical techniques, such as the cutting speed.

Although various aspects of the invention, such as the use of sharpened and/or coated electrodes and various generator power curves and profiles, have previously been used in the art, the combination of i) the blade geometry disclosed herein, ii) the generator power profile disclosed herein, and iii) the automated high speed monitoring and control by the generator circuitry of the output parameters of the generator have been found to produce significantly improved performance in cutting efficiency, dramatic reduction in unwanted tissue damage, and improved post-operative recovery to the point that the invention rivals the performance of mechanical surgical scalpels.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the present invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

The present invention relates to the use of a shaped electrosurgical electrode tip with a customized power curve. More specifically, the present invention relates to using an electrosurgical electrode tip having a sharpened working surface and a limited mass/thickness, and applying a customized power curve produced by a wave generator to the electrosurgical electrode tip in order to introduce and/or enhance properties, characteristics and/or attributes at the working surface.

The following disclosure is grouped into four subheadings, namely "Exemplary Operating System," "Electrode Tip Geometry," "Customized Power Curve," and "Clinical Trial Examples." The utilization of the subheadings is for convenience of the reader only and is not to be construed as limiting in any sense.

Exemplary Operating System

Figure 1:
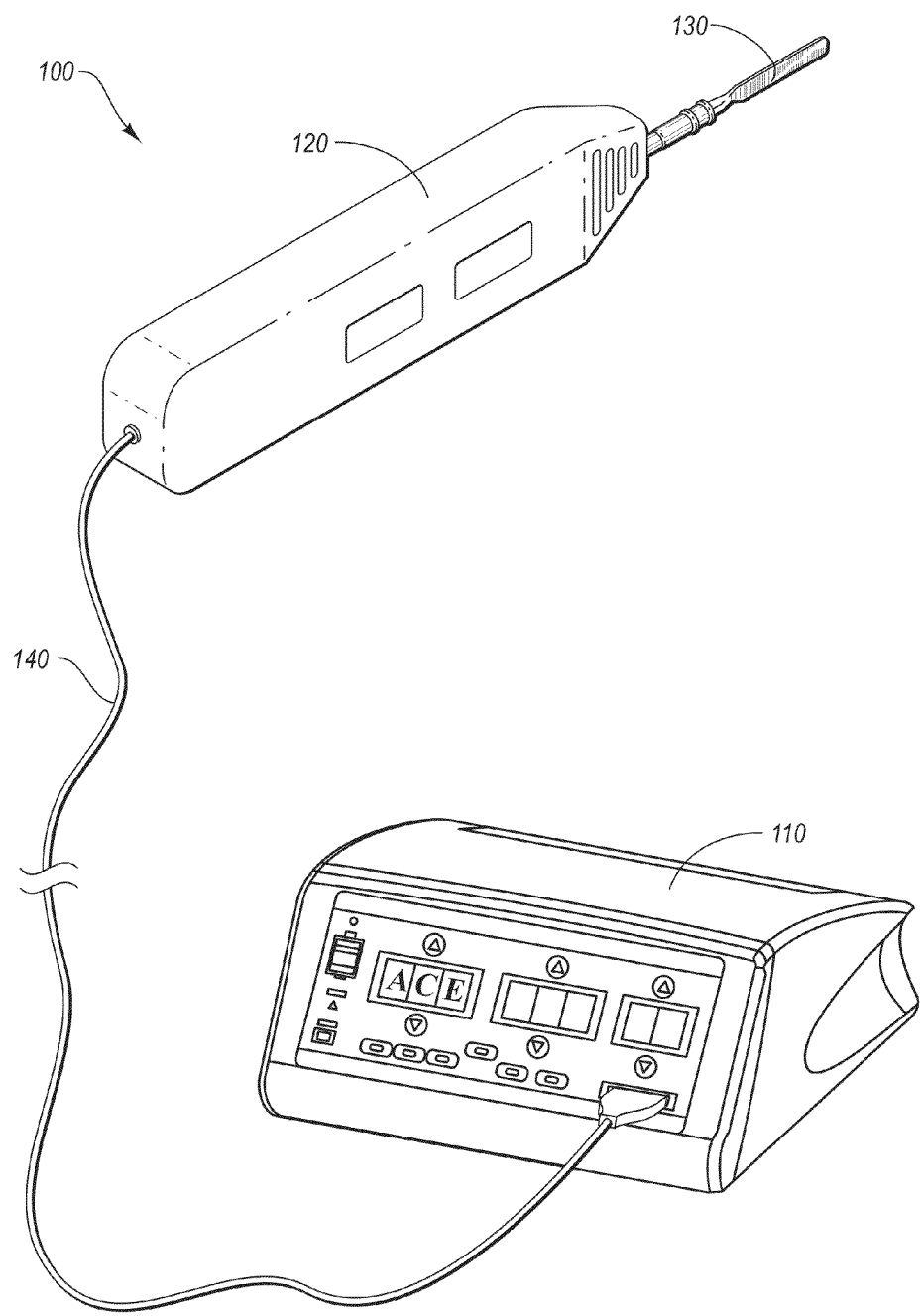
FIG. 1 illustrates an exemplary electrosurgical system according to the present invention.

FIG. 1 and the corresponding discussion are intended to provide a brief, general description of an operating system in which one embodiment of the invention may be implemented. Although not required, the invention will be described in the general context of providing specific properties, attributes and/or characteristics to an electrosurgical electrode and a working surface thereof, and applying a customized power curve to the electrosurgical electrode tip in order to improve the quality of electrosurgical operations and limit damage to the tissue of a patient resulting from electrosurgery. Those skilled in the art, however, will appreciate that embodiments of the present invention may be practiced in association with a variety of different surfaces and power curves in order to provide desirable properties, attributes and/or characteristics during electrosurgery.

Referring to FIG. 1, an exemplary system is illustrated that can include the features of the present invention. In FIG. 1, electrosurgical system 100 is illustrated, which includes a wave generator 110, a hand-held electrode 120, and an electrode tip 130. Generator 110, in a preferred embodiment, is an RF wave generator. A surgeon may use electrosurgical system 100 during surgical procedures to cut tissue and/or cauterize blood vessels of a patient's body.

In electrosurgery, radio frequency (RF) electrical energy is produced by a wave generator, such as wave generator 110, and is introduced to a patient's body by a hand-held electrode, such as electrode 120, which is electrically coupled to wave generator 110 and includes electrode tip 130. Wave Generator 110 can include a high-frequency oscillator and amplifiers to generate an RF electrical energy wave that can be used to cut tissue and/or cauterize blood vessels during electrosurgery. The RF electrical energy wave powers electrode 120 and is transmitted from wave generator 110 to electrode 120 via cord 140. An electrical discharge is delivered from electrode tip 130 to the patient in order to cause the heating of cellular matter of the patient that is in extremely close contact to electrode tip 130. The heating takes place at an appropriately high temperature to allow electrode 120 to be used to perform electrosurgery. A grounding electrode (not shown) provides a return electrical path to wave generator 110 for any excess charge that is dissipated into surrounding tissue of the patient's body.

During electrosurgery, electrode 120 may be used to independently or concurrently cut and cauterize. A constant sinusoidal wave supplied by wave generator 110 and transmitted to electrode 120 allows electrode tip 130 to cut through tissue of the patient's body. Alternatively, a damped wave supplied by wave generator 110 and transmitted to electrode 120 allows electrode tip 130 to cauterize leaking blood vessels. A combination of the constant sinusoidal wave and the damped wave can be supplied by wave generator 110 to electrode 120 for allowing electrode tip 130 to concurrently cut and cauterize, thereby minimizing tissue trauma and blood loss during the surgical procedure.

Electrode Tip Geometry

FIGS. 2-11 illustrate an exemplary assortment of interchangeable electrode tips, including a standard electrode tip, a shaped electrode tip with sharpened working surfaces, a scalpel-type electrode tip, a needle electrode, a modified ball electrode, and various laparoscopic electrodes, for use with a conventional electrosurgical holder, such as hand-held electrode 120 seen in FIG. 1, to facilitate the acts of cutting tissue and/or cauterizing blood vessels. Each of the interchangeable electrode tips has a connection end that can be coupled to the hand-held electrode 120 to allow RF electrical energy generated by wave generator 110 to be transmitted through hand-held electrode 120 to the electrode tip. The lengths of the connection ends of the various electrode tips can vary depending on the specific type of electrode tip and/or the type of procedure for which the electrode tip is used. For instance, the lengths of the connection ends may range from about 6.35 cm to about 48 cm. In some embodiments, the lengths of the connection ends are about 6.35 cm, 6.9 cm, 10.16 cm, 15.24 cm, 33 cm, 45 cm, and 48 cm. It will be appreciated that the lengths of the connection ends can be any suitable lengths and are not intended to limit the scope of the present invention.

Each of the illustrated electrode tips also includes a working end that applies the electrical discharge to the patient's body. A sleeve or coating can surround at least a portion of the electrode tip to act as an insulator, provide protection, and facilitate holding of the electrode tip by hand-held electrode 120. For example, an insulative material can be applied to a potion of the working end of the electrode tip in order to provide an insulative barrier between a portion of the working end and a patient's tissue. In one embodiment, the insulative material is applied around the working end of the electrode tip, leaving only a small part of the electrode tip exposed for use during electrosurgery. For example, the insulative material may cover the entire working end except for about 0.3 cm at the end of the electrode tip. The exposed portion can then be used to perform electrosurgery without electrical discharge between the rest of the working end and the patient's tissue. In one embodiment, the coating can comprise a PARYLENE material. PARYLENE materials are poly(p-xylylene) polymers that are chemical vapor deposited and which provide both a moisture barrier and electrical insulative properties. A PARYLENE material can be applied, for example, to a portion of the working end of the electrode tip in order to provide an insulative barrier between a portion of the working end and a patient's tissue.

The working ends of the illustrated electrodes can be configured to provide great versatility in cutting and/or cauterizing tissue and/or blood vessels in a variety of different surgical procedures. Furthermore, the electrode tips can be configured to produce significantly improved performance in cutting efficiency, dramatic reduction in unwanted tissue damage, and improved post-operative recovery. For instance, each of the electrode tips illustrated in FIGS. 2-11 includes or could be formed with one or more shaped or sharpened working edges. As described in greater detail below, the shaped working edges concentrate the electrical energy transferred from the electrode tip to the patient's tissue. The concentrated electrical energy reduces the amount of extraneous charge loss into surrounding tissue, thereby reducing the amount of necrotic damage in the tissue surrounding the incision site. Similarly, each of the illustrated electrode tips is or could be formed with a limited thickness and/or mass to limit the amount of latent heat or thermal energy that can build up in the electrode tip. As discussed below, reducing the amount of latent heat within the electrode tip reduces the amount of latent heat that is transferred from the electrode tip to the tissue, which reduces the amount of tissue damage caused in tissue surrounding the incision site.

Turning to FIGS. 2-11, various aspects of each of the illustrated electrode tips will now be described. As noted above and identified below in connection with the embodiments illustrated in FIGS. 2-11, each of the electrode tips can include one or more shaped or sharpened surfaces. While these shaped/sharpened surfaces are identified in connection with the discussion of FIGS. 2-11, a more detailed discussion of the features and parameters applicable to each of these shaped/sharpened surfaces, regardless of the overall configuration of the particular electrode tip, will follow the discussion of the individual electrode tip embodiments. Additionally, a more detailed discussion of the mass/thickness aspects applicable to each of the illustrated electrode tips will follow the discussion of the features and parameters applicable the shaped/sharpened surfaces.

Figure 2:
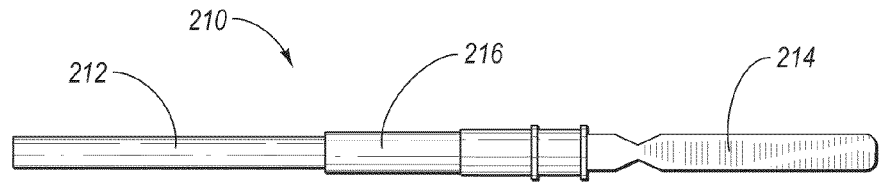
FIG. 2 illustrates an exemplary electrosurgical electrode tip for use with the electrosurgical system of FIG. 1 to cut tissue and cauterize blood vessels in general surgery.

FIG. 2 illustrates electrode tip 210, which is an electrode tip that may be used in general surgery for cutting tissue and/or for cauterizing blood vessels. Electrode tip 210 includes connection end 212 for coupling electrode tip 210 to hand-held electrode 120. Electrical discharge is delivered to the patient's body from working end 214, which is in a standard electrode blade-like configuration. In this illustrative configuration, working end 214 has two parallel sides that are flat to allow working end 214 to function in a similar manner as a traditional scalpel; however, working end 214 can have various other configurations as known to those skilled in the art, including but not limited to sharpened sides or partially sharpened sides (as discussed below with reference to FIGS. 3-7, for example). In the illustrated configuration, rather than employing a mechanical action for cutting through tissue, the electrical discharge allows working end 214 to slide through the tissue as the tissue is being superheated to an appropriate temperature to perform the electrosurgical procedure. Electrode tip 210 also includes a coating or sleeve 216 that surrounds at least a portion of tip 210.

Figure 3:
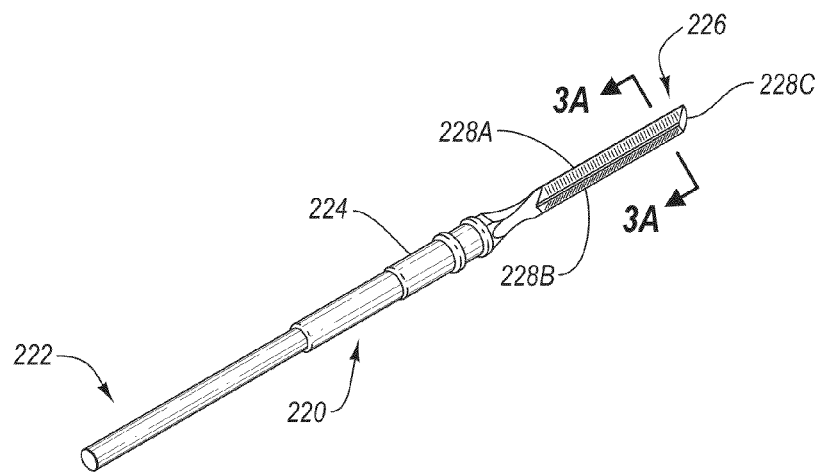
FIG. 3 is a perspective view of an electrosurgical electrode tip embodying principles according to the present invention.
Figure 3A:
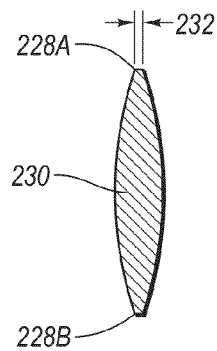
FIG. 3A is a cross-sectional end view of the electrosurgical electrode tip of FIG. 3A depicting a sharpened working surface.

FIG. 3 depicts an electrode tip similar to that shown in FIGS. 1 and 2. Thus, in FIG. 3 there is seen an electrosurgical electrode 220 having a connection end 222 fitted with a sleeve fitting 224 positioned around the electrode shank to provide protection and to facilitate holding of the electrode by a conventional electrosurgical holder as seen in FIG. 1. The electrode also includes a working end 226 that is formed with a shaped or sharpened geometry. The embodiment illustrated in FIG. 3 features a cross sectional geometry which includes two opposing edges 228A and 228B that are sharpened as shown in FIG. 3A. In addition, working end 226 can also include an edge 228C that has a similar cross sectional shape as edges 228A and 228B. Edges 228A, 228B, and 228C can be used to cut tissue and/or cauterize blood vessels during an electrosurgical procedure.

FIG. 3A is a sectional view of working end 226 of electrode tip 220 taken along the section lines 3A-3A of FIG. 3. Electrically conductive main body 230 may be of any suitable material such as, preferably, surgical grade stainless steel. Body 230 has been sharpened at two opposing surfaces to edges 228A and 228B, each of which, as described in more detail below in connection with FIGS. 12-14, concentrates or focuses the electric field created when electrical potential is applied to the electrode tip, thus increasing the concentration of transferred electrical energy and correspondingly improving efficiency with which the implement achieves a cutting action, e.g., severs tissue, and reducing the amount of extraneous charge loss in tissue which is not in close proximity to the point or sharpened edge. Furthermore, as also discussed in greater detail below, sharpening at least one of the working edges of the electrode tip also reduces the mass of the electrode tip. The reduced mass limits the amount of latent heat transferred to the surrounding tissue, thereby reducing the tissue depth of necrosis associated with the electrosurgical process.

Figure 4:
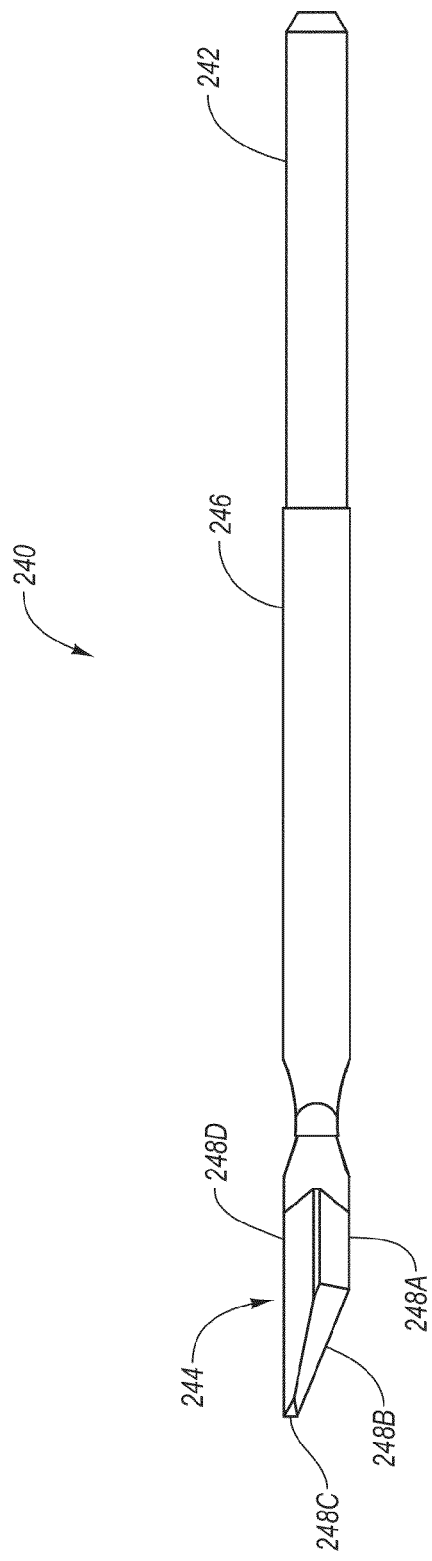
FIG. 4 is a perspective view of a scalpel-type electrosurgical electrode tip according to an exemplary embodiment of the present invention.

Turning now to FIG. 4, there is seen an electrode tip 240 which can also be used in general surgery for cutting tissue and/or for cauterizing blood vessels. Electrode tip 240 includes connection end 242 and working end 244. Working end 244 is in a scalpel-like blade configuration that has a profile that resembles a mechanical scalpel and which is further described below. Electrode tip 240 also includes an insulative sleeve or coating 246 to provide protection and to facilitate holding of electrode tip 240 by hand-held electrode 120.

Similar to electrode tip 220 illustrated in FIGS. 3 and 3A, electrode tip 240 includes multiple shaped or sharpened working edges 248A, 248B, 248C, and 248D. Working edges 248A, 248B, 248C, and 248D have similar cross-sectional shapes as edges 228A, 228B, and 228C described above. More specifically, working edges 248A, 248B, 248C, and 248D are shaped or sharpened to concentrate or focuses the electric field created when electrical potential is applied to electrode tip 220. As noted, the details of the shaping or sharpening of the working edges will be discussed in more detail below with reference to FIGS. 12-14.

Because cutting with working edges 228A, 228B, 228C, 248A, 248B, 248C, and 248D is effectuated as a result of the concentration of electrosurgical energy rather than the sharpness of a normal mechanical scalpel, an electrode according to the present invention is safer to handle than a scalpel because the working edges of the electrode are not required to be as sharp as a mechanical scalpel, thus reducing the risk of a mechanical cut to a physician or other operating room personnel while handling the electrode.

As can be seen in FIG. 4, working edges 248A, 248B, 248C, and 248D are formed with differing lengths and can be angled relative to one another. The differing lengths and orientation of working edges 248A, 248B, 248C, and 248D in the illustrated embodiment gives working end 244 a profile resembling a mechanical scalpel. The scalpel-like profile allows for great versatility when using electrode tip 240. The differing lengths and orientation of the working edges can allow a surgeon to make many different types of incisions and cauterize large or small areas with a single electrode tip. For instance, the inclusion of a shorter working edge and a longer working edge in a single electrode enables a surgeon to use the same electrode to create different types of incisions during a single procedure without having to change electrodes. Rather, the surgeon can simply rotate the electrode to utilize the desired working edge.

By way of non-limiting example, working edge 248A can be sized to make relatively shallow and/or delicate incisions in a patient's skin. The length of working edge 248A can also help prevent a surgeon from inadvertently cutting too deep. Once the shallow incision is made, the surgeon can then rotate electrode tip 240 by 180° and use working edge 248D to make a deeper incision, such as in a subcutaneous layer. In one embodiment, working edge 248A is about 3 mm long and working edge 248D is about 8 mm long. In another embodiment, working edge 248A is about 4 mm long and working edge 248D is about 11 mm long. Other lengths and combinations can also be used for the different working edges. Additionally, working edge 248C can be sized to enable a surgeon to cut and/or cauterize a very small area without having to replace electrode tip 240 with a needle electrode, for example. In one embodiment, working edge 248C is about 0.5 mm long. It will be appreciated that electrode tip 240 can be formed with fewer or more working edges 248. Thus, the shape and size of working edge 248C can provide the ability to perform nearly pinpoint incisions and/or coagulation.

Figure 5:
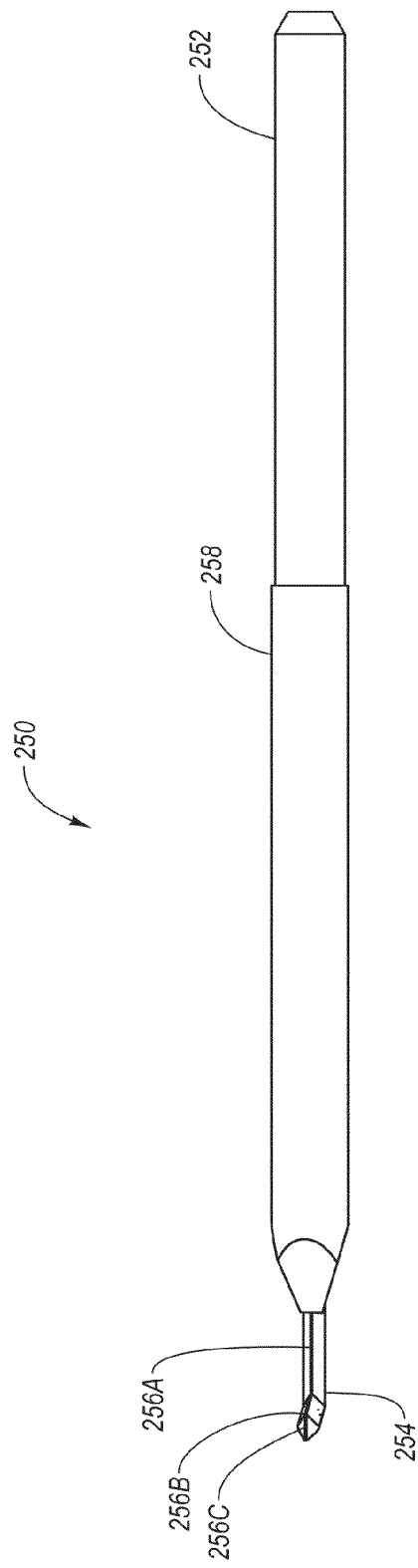
FIG. 5 is a perspective view of an L-hook electrosurgical electrode tip according to an exemplary embodiment of the present invention.

FIG. 5 illustrates electrode tip 250, which is an electrode tip that may facilitate a surgeon in reducing extraneous tissue damage by allowing individual tissues or blood vessels to be isolated and independently cut and/or cauterized. Electrode tip 250 includes connection end 252 and working end 254. Working end 254 is in an L-hook configuration. Working end 254 has three working edges 256A, 256B, and 256C, each of which is shaped or sharpened as described herein. It will be appreciated that electrode tip 250 can be formed with fewer or more working edges 256. As with the other electrode tips, electrode tip 250 includes a coating or sleeve 258 that surrounds at least a portion of electrode tip 250 to act as an insulator, provide protection, and facilitate holding of electrode tip 250.

Figure 6:
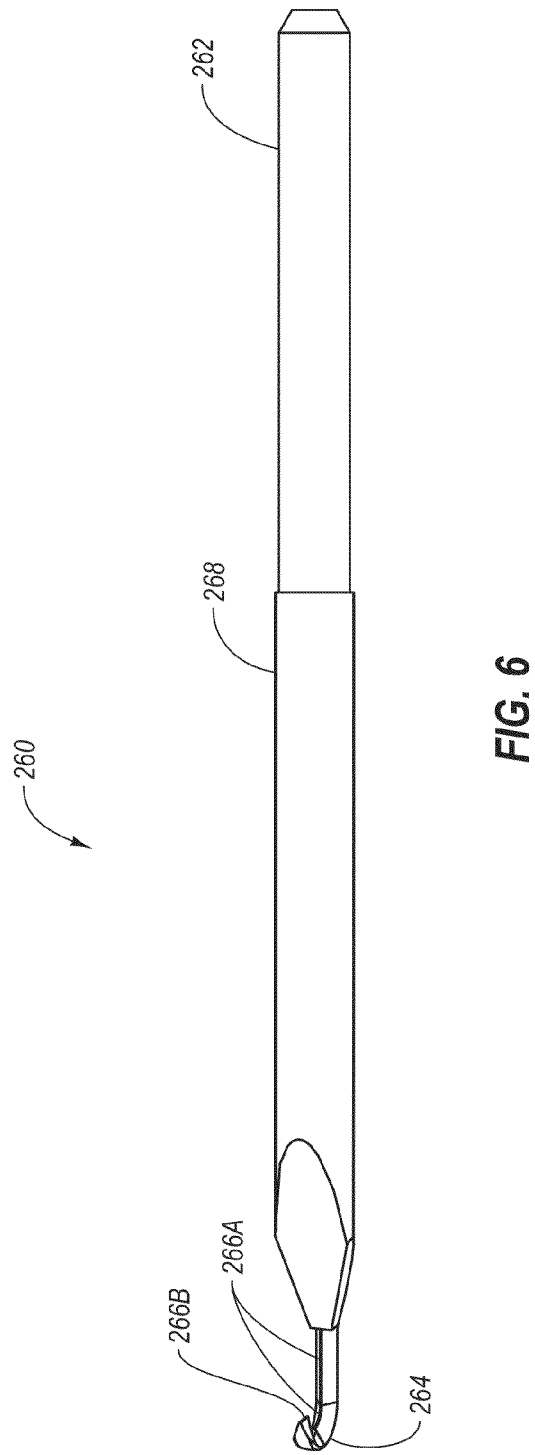
FIG. 6 is a perspective view of a J-hook electrosurgical electrode tip according to an exemplary embodiment of the present invention.

FIG. 6 illustrates electrode tip 260 that is similar to electrode tip 250. Electrode tip 260 includes connection end 262 and working end 264. Working end 264 is in a J-hook configuration and has two working edges 266A and 266B, each of which is shaped or sharpened as described herein. Electrode tip 260 can be formed with fewer or more working edges 266 and also includes a coating or sleeve 268 that surrounds at least a portion of electrode tip 260.

Figure 7:
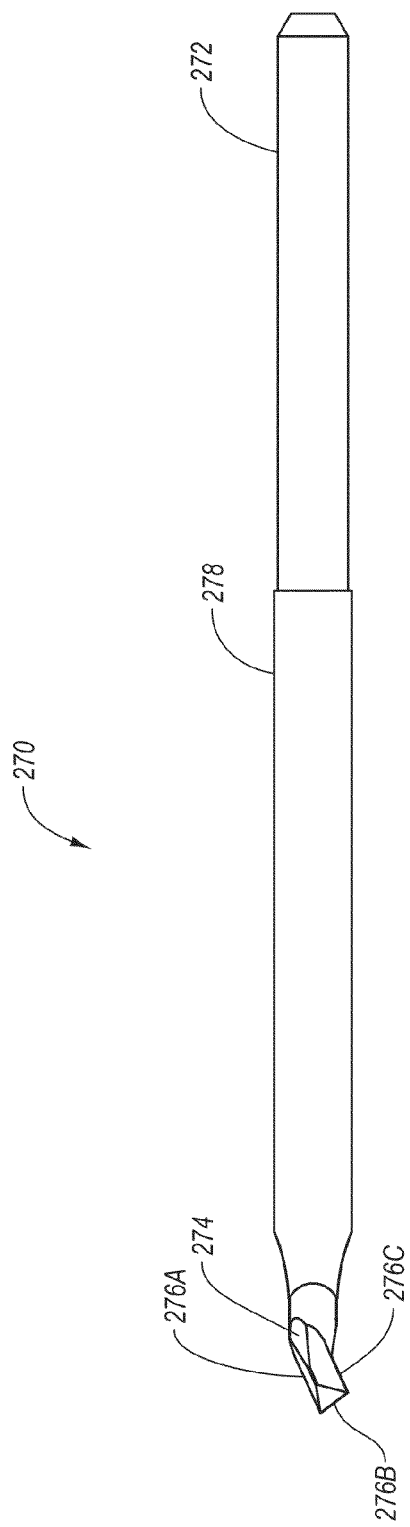
FIG. 7 is a perspective view of another electrosurgical electrode tip embodying principles according to the present invention.

FIG. 7 illustrates electrode tip 270 that includes connection end 272 and working end 274. Working end 274 has three working edges 276A, 276B, and 276C, each of which is shaped or sharpened as described herein. Electrode tip 270 can be formed with fewer or more working edges 276. As with the other electrode tips, electrode tip 270 includes a coating or sleeve 278 that surrounds at least a portion of electrode tip 270 to act as an insulator.

Figure 8:
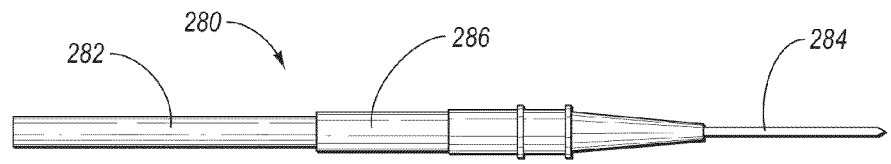
FIG. 8 illustrates an exemplary needle-type electrosurgical electrode tip for use in the suitable operating system of FIG. 1 to cut tissue and cauterize blood vessels in particularly dense areas.

FIG. 8 illustrates electrode tip 280, which is an electrode tip that may be used for cutting tissue and cauterizing leaking blood vessels in particularly dense areas of a patient's body, such as those experienced in cerebral operations. Electrode tip 280 includes connection end 282 and working end 284. Working end 284 is in a needle-like configuration that comes to a point to allow for very accurate surgical procedures in dense areas of the patient's body. The tip and/or sides of working end 284 can be shaped or sharpened as described herein. Furthermore, electrode tip 280 includes a coating or sleeve 286 that surrounds at least a portion of tip 280. Through the use of electrode tip 280, delicate cerebral tissues can be accurately removed with virtually no damage to any surrounding membranes and with minimal bleeding and/or swelling resulting from the procedure.

Figure 9:
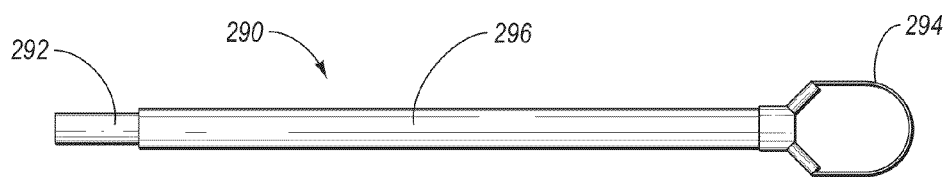
FIG. 9 illustrates an exemplary electrosurgical electrode tip for use in the suitable operating system of FIG. 1 to remove large sections of tissue.
Figure 10:
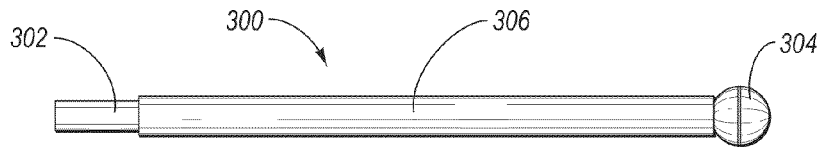
FIG. 10 illustrates an exemplary electrosurgical electrode tip for use in the suitable operating system of FIG. 1 to cauterize leaking blood vessels and to seal open structures.
Figure 11:
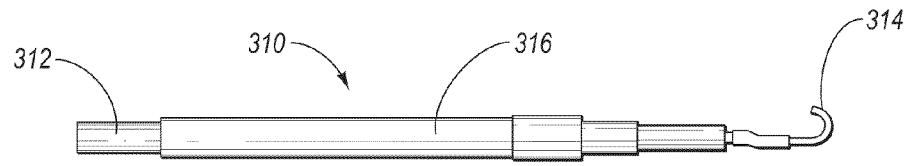
FIG. 11 illustrates an exemplary electrosurgical electrode tip for use in the suitable operating system of FIG. 1 to isolate tissue and to independently cut or cauterize.

FIGS. 9-11 illustrate additional electrode tips that can be used in connection with electrosurgical system 100. While the electrode tips of FIGS. 9-11 are not illustrated has having a sharpened working edge, it will be appreciated that each of the electrode tips illustrated in FIGS. 9-11 can be formed with one or more sharpened working edges as described herein.

FIG. 9 illustrates electrode tip 290, which is an electrode tip that may be used for the removal of large sections of tissue, as in, for example, prostate and tumor excision. Connection end 292 is coupled to the hand-held electrode while working end 294 is used to delivered electrical energy to the patient's body. Working end 294 is in a loop-like configuration. A coating or sleeve 296 can surround at least a portion of electrode tip 290.

FIG. 10 illustrates electrode tip 300, which is an electrode tip that may be used to specifically cauterize leaking blood vessels and to seal open structures. Electrode tip 300 includes connection end 302 and a spherical working end 304. A coating or sleeve 306 can surround at least a portion of electrode tip 300.

FIG. 11 illustrates electrode tip 310, which is an electrode tip that may facilitate a surgeon in reducing extraneous tissue damage by allowing individual tissues or blood vessels to be isolated and independently cut and/or cauterized. Electrode tip 310 includes connection end 312 and a hook-like working end 314. A sleeve or coating 316 can surround at least a portion of electrode tip 310.

Figure 12:
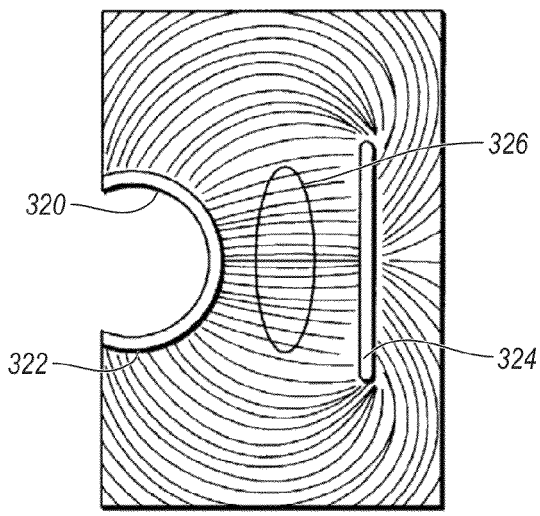
FIG. 12 is a schematic representation of a typical electric field existing between a rounded surface implement and a working return electrode.
Figure 13:
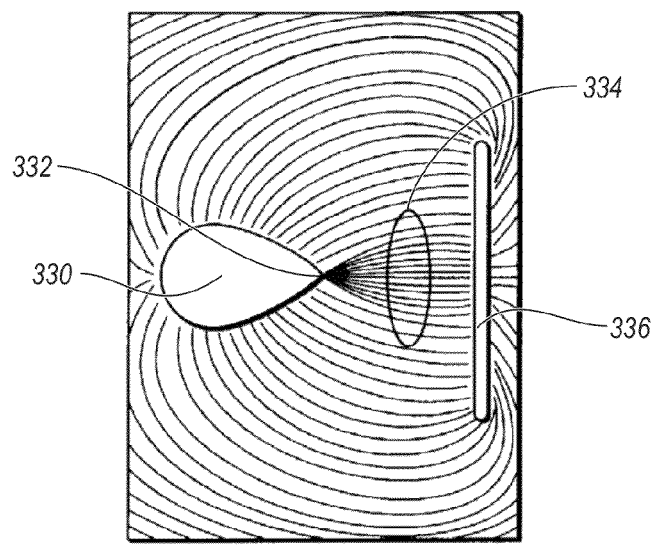
FIG. 13 is a schematic representation of a modified electric field concentration associated with an implement having sharpened edge.

As noted, each of the above-described electrode tips includes or can be formed with one or more shaped or sharpened working edges. As also noted, theses shaped working edge concentrate the electrical discharge from the electrode tip, thereby reducing the amount of extraneous charge loss in tissue which is not in close proximity to the point or sharpened edge. The physical principles underlying the foregoing marked improvement can be understood from reference to FIGS. 12-14. FIG. 12 is a diagram illustrating electric field pattern lines for an electric field existing between a conductor or electrode tip 320 having an annular, or curved, exterior surface 322 and a counter electrode 324. Although electrode 320 is shown in FIG. 12 as being hollow, the electric field pattern shown will be essentially the same if the electrode were solid. It will now be seen that the density of the electric field lines within ellipse 326 are nearly uniform and thus the electric field does not vary substantially within that region. However, in FIG. 13, it will be noted that if the geometry of electrode 330 is made to include a pointed region as represented by point or edge 332, the corresponding electric field becomes much more concentrated as represented by the much greater line density of electric field lines (within the ellipse 334) between the electrode 330 and counter electrode 336. Thus, on an irregularly shaped conductor, charge tends to accumulate at locations where the curvature of the surface is greatest, that is, at sharp points or edges. By sharpening the blade edge, the charge is concentrated along a much smaller surface area or region thus focusing the electric field lines into a tighter arrangement which reduces extraneous charge loss in tissue which is not in close proximity to the point or sharpened edge. The cutting edge of the electrode need not be sharply pointed, it need only be shaped (sharpened) to concentrate energy transfer to the degree desired for optimum cutting.

By way of illustration, a conventional unsharpened electrode has an edge thickness of about 0.33 mm and in a typical cutting mode may utilize a power setting nearing 50 watts. When sharpened to an edge thickness of about 0.00735 mm, a "sharpness" below that required of a mechanical scalpel blade, the electrodes of FIGS. 3-11 can quickly cut through tissue at less than 20 watts, a power setting of 50% less than that required for typical unsharpened electrode. Moreover, such blades cut more rapidly with less resistance, less eschar production, less thermal necrosis, and improved operator control.

Figure 14:
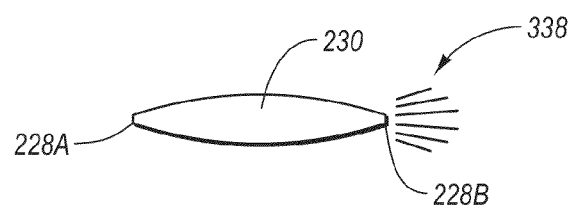
FIG. 14 is a simplified schematic representation of a typical concentration of electric field projected from the sharpened edge of FIG. 3A.

The foregoing principles are illustrated in FIG. 14. As noted above, FIG. 14 is a simplified view illustrating a typical concentration of electric field projected from a sharpened edge 228B of electrode 220 illustrated in FIGS. 3 and 3A. To facilitate clarity and simplicity of presentation, only lines 338 representing the electric field in the direction of the sharpened point or edge 228B are shown.

It will be observed that the electrode of FIG. 14 is that earlier illustrated in FIG. 3A. Thus, there is shown electrically conductive main body 230 with sharpened edges or points 228A and 228B. When electrosurgical potential is applied to body 230 in the presence of tissue for which severance is desired, the density of energy transfer is concentrated at the apex 228B as represented by the longer rays within bundle of rays 338. Thus, in the illustrated example, energy is concentrated along the principal axis of main body 230 extending from edge 228B. It will be appreciated that electrode tip 320 is used by way of example, and the present discussion is applicable to the sharpened working edges(s) of each of the above-described electrode tips. It should also be understood that while the preferred geometry of electrode tips embody at least one fully sharpened edge (or point), the efficacious characteristics flowing from the invention begin to be significantly observed when the dimension of the working edge width (i.e., the width 232 of working edge 228A in FIG. 3A, for example) is generally between 0.0254 mm and 0.1270 mm, more preferably between 0.076 mm and 0.1270 mm, and most preferably 0.1016 mm.

In addition to the above dimensions for a working surface of an electrode tip, following is a further discussion of how a shaped or sharpened electrode tip reduces the amount of undesirable tissue damage around an incision site. As noted herein, a shaped or sharpened electrode tip concentrates the electric field at the shaped or sharpened edge of the electrode tip, thereby creating a stronger electric field than is present with a standard electrode tip. This stronger electric field causes a rapid rise in the temperature at the surface of the electrode tip. Rapidly increasing the temperature at the surface of the electrode tip causes a corresponding rapid temperature rise in the tissue that is in very close proximity to the electrode tip. The rapid increase in the tissue temperature adjacent the electrode tip causes a narrower depth of the tissue to rapidly reach coagulation. As discussed elsewhere herein, electrosurgical system 100 can quickly and automatically reduce the electrosurgical current flowing through the electrode tip once the tissue that is in close proximity to the electrode tip reaches coagulation. Rapidly reducing the electrosurgical current prevents the temperature of the tissue surrounding the incision site from rising high enough to cause necrosis.

Figure 15:
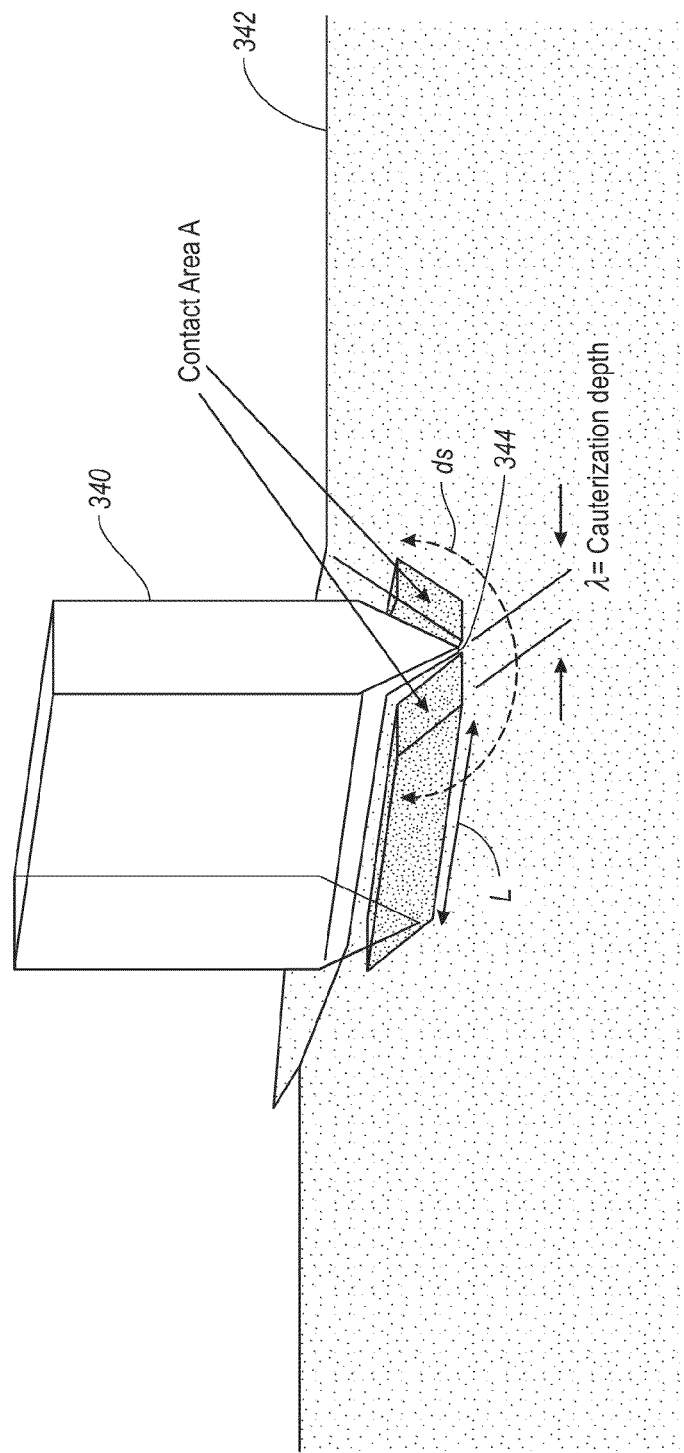
FIG. 15 illustrates an sharpened electrode tip cutting through the tissue of a patient and the area affected by the electrode tip.

Reference is now made to FIG. 15, which illustrates a simplified electrode tip 340 being used to cut tissue 342. Electrode tip 340 includes a shaped/sharpened working edge 344 that concentrates or focuses the electric discharge between electrode tip 340 and tissue 342 during electrosurgery as described herein. During the performance of electrosurgery, an impedance R arises between electrode tip 340 and tissue 342. The impedance R can be defined by:

$$R = \frac{\rho_c \lambda}{A} \qquad \text{Equation 1}$$

where $\rho_c$ is the bulk resistivity of tissue 342, $\lambda$ is the cauterization depth, or depth of tissue affected by the electrosurgical procedure, and A is the area over which the electrosurgery occurs. The area A is equal to L×ds, where L is the length of electrode tip 340 that is in contact with tissue 342 and ds is distance around working edge 344 that is in contact with tissue 342. Sharpening electrode tip 340 reduces the value of ds, which in turn reduces the contact area A compared to using a standard electrode tip.

As is well know, the bulk resistivity of tissue $\rho_c$ is tissue dependant. Tissues can be broadly categorized according to bulk resistivity $\rho_c$ into one of four groups: very high resistivity, high resistivity, medium resistivity, and low resistivity. Example of tissues that fall within each of these categories include scar tissue (very high resistivity), adipose tissue (high resistivity), abdominal tissue (medium resistivity), and muscular tissue (low resistivity). Further, the bulk resistivity $\rho_c$ of tissue is also temperature dependent. As the temperature of the tissue $T_t$ rises, the bulk resistivity of the tissue $\rho_c$ decreases until a critical desiccation temperature $T_d$ is reached. When the tissue temperature rises above the desiccation temperature $T_d$, the resistivity of the tissue $\rho_c$ begins to rapidly increase. The rapid increase in the tissue bulk resistivity $\rho_c$ can therefore be used as an indication of the completion of the electrosurgical process. The temperature dependence of the tissue bulk resistivity $\rho_c$ can be defined by:

$$\rho_c = \rho_{c0} + f(T) \qquad \text{Equation 2}$$

where $\rho_{c0}$ is the initial tissue resistivity and f(T) is a function of temperature.

From Equations 1 and 2 it can be seen that the impedance R is temperature dependent because of its dependence on the temperature dependent tissue bulk resistivity $\rho_c$. Consequently, the rate at which the impedance R changes as a result of the changing temperature can be defined as:

$$\frac{\partial R}{\partial T} = \frac{\lambda}{A} \frac{\partial \rho_c}{\partial T} \qquad \text{Equation 3}$$

This relationship reveals that, with a shaped or sharpened working edge 344, the smaller contact area A increases the change of impedance of the tissue for the same temperature change $\partial T$. The larger change in impedance over the same temperature change allows the electrosurgical generator to more quickly detect when the tissue has reached the desiccation temperature $T_d$. This quicker and stronger feedback to the electrosurgical generator results in a faster reduction in the power when the tissue begins to desiccate, thereby resulting in a faster reduction in the total power applied to the tissue when the tissue is desiccated. The power reduction features of the present invention will be discussed in greater detail below. Nevertheless, it should be understood from this discussion that the stronger the feedback mechanism, the faster the power can be reduced, which advantageously minimizes the depth $\lambda$ of damage to the tissue surrounding the incision site.

The combination of the sharpened electrode tip and the quick reduction in the output power supplied by the electrosurgical generator (discussed in detail below) provide a fast feedback mechanism that automatically corrects/regulates the electrosurgical technique and substantially reduces the depth of necrotic tissue damage. The effects of the sharpened electrode tip and adjustable power output combination are further enhanced when the mass of the electrode tip is limited. As noted above, the amount of latent heat that can be retained by an electrode tip is directly related to the mass of the electrode tip. More latent heat can be retained by larger mass electrode tips than by smaller mass electrode tips. Thus, limiting the mass of the electrode tip limits the amount of latent heat that the electrode tip is able to retain.

The latent heat that can build up in an electrode tip during an electrosurgical procedure can be transferred to the tissue around to the electrode tip. This transfer of thermal energy can cause undesirable necrotic damage in the tissue surrounding the incision site and not just at the incision site. Therefore, reducing the mass of the electrode tip also reduces the amount of latent heat that the electrode tip can transfer to the surrounding tissue, thereby reducing the amount of undesirable tissue damage surrounding the incision site. While low mass electrode tips still transfer latent thermal energy to surrounding tissue, the amount of latent thermal energy that a low mass electrode tip transfers to the surrounding tissue is relatively small compared to the amount of energy from the electrical discharge that is expended to cauterize the tissue during the electrosurgical procedure. Thus, to further enhance the effects of the sharpened electrode tip and adjustable power output combination, the mass of the electrode tip can be limited to further reduce the amount of excessive and undesirable tissue damage surrounding the incision site.

In order to determine how thin a stainless steel electrode tip needs to be in order to limit the tissue damage caused by the build up of excessive latent heat, we begin by equating the thermal energy of the stainless steel electrode tip at a temperature $T_B$ with the thermal energy of the tissue area at a temperature $T_t$. Determining the maximum desired thickness of the electrode tip as follows ensures that the latent heat from the electrode tip will only cause the tissue temperature $T_t$ to raise enough to cause homeostasis in the area of the tissue that is in close proximity to the electrode tip. In other words, limiting the thickness of the electrode tip according to the following calculations will limit the build up of latent heat within the electrode tip that would otherwise cause undesired necrotic damage deeper into the tissue surrounding the incision site.

Equating the thermal energy of the electrode tip and the tissue provides:

$$\lambda \partial T_t \rho_t C_t = \partial T_B \rho_B C_B W_B \qquad \text{Equation 4}$$

In Equation 4, $C_B$, $\rho_B$, and $W_B$ are, respectively, the heat capacity, density, and thickness of the steel electrode tip, and $C_t$, $\rho_t$, and $\lambda$ are, respectively, the heat capacity, density, and cauterization depth of the tissue. By rearranging Equation 4 it can be seen that:

$$\lambda \partial T_t = \partial T_B \frac{\rho_B}{\rho_t} \frac{C_B}{C_t} W_b \qquad \text{Equation 5}$$

It is known that the heat capacity $C_B$ and density $\rho_B$ of steel are, respectively, about $$0.42 \frac{kJ}{kgC} \text{ and } 7850 \frac{kg}{m^3}.$$

It is similarly known that the heat capacity $C_t$ and density $\rho_t$ of tissue are, respectively, about $$0.42 \frac{kJ}{kgC} \text{ and } 7850 \frac{kg}{m^3}.$$

Using these values, Equation 5 reduces to:

$$\lambda \partial T_t = 0.78 \partial T_B W_b \qquad \text{Equation 6}$$

By inserting typical temperature change values experienced during electrosurgery in the tissue and the electrode tip, Equation 6 can be rearranged to find the thickness of the steel electrode tip $W_B$ as a function of the cauterization depth of the tissue $\lambda$. During electrosurgery, the tissue temperature typically rises about 50-100 C. and the electrode tip temperature typically rises about 250-350 C. Thus, the thickness of the electrode tip should be:

$$W_B \leq \frac{\lambda}{3} \qquad \text{Equation 7}$$

As discussed herein, it is desirable to minimize the depth of tissue damage experienced around an incision site. It is therefore preferable to minimize the cauterization depth $\lambda$, while still effectively causing homeostasis at the incision site. An acceptable cauterization depth is about 0.5 mm. Therefore, in order to prevent excessive tissue damages as a result of latent heat buildup in the electrode tip, Equation 7 and the acceptable cauterization depth of 0.5 mm can be used to determine that the thickness of the electrode tip should be about 0.17 mils (0.4318 mm) or less. From the discussion herein, it will be readily apparent to one of ordinary skill in the art that electrode tips with thinner dimensions than 0.17 mils (0.4318 mm) will further reduce the amount of tissue damage caused by the latent heat of the electrode tip. As noted above, for instance, the efficacious characteristics flowing from the invention can be significantly observed when the electrode tip has a dimension generally between 0.0254 mm and 0.1270 mm, more preferably between 0.076 mm and 0.1270 mm, and most preferably 0.1016 mm.

In addition to limiting the thickness/mass of the electrode tip and sharpening a working surface of ends 214, 226, 244, 254, 264, 274, 284, 294, 304, and 314, at least a portion of ends 214, 226, 244, 254, 264, 274, 284, 294, 304, and 314 can be coated to provide one or more desirable attributes and/or properties at the working surface. Such desirable properties and/or attributes can include a high temperature stability to withstand the temperatures of electrosurgery and a flexibility to increase the durability of the electrode tip. Additionally, a non-stick coating can serve to eliminate or reduce the clinging of charred tissue to the blade, thereby reducing incidences of unwanted tissue damage. A non-stick material suitable for use as a coating on ends 214, 226, 244, 254, 264, 274, 284, 294, 304, and 314 can be, but is not limited to, PTFE or a hybrid material that can include a combination of at least one of an organic material and an inorganic material, and that provides the coated surface with desirable properties, such as a high temperature stability, flexibility, and a low temperature application condition so that the coating layer may me applied by a spray or dip process. An example of a hybrid coating is provided in U.S. Pat. No. 6,951,559, entitled "Utilization of a Hybrid Material in a Surface Coating of an Electrosurgical Instrument" that issued on Oct. 4, 2005 to Greep, the disclosure of which is incorporated herein by reference in its entirety.

Customized Power Curve

Electrosurgical wave generators are well known in the art. Wave generators commonly include a high-frequency oscillator and amplifiers that generate RF electrical energy that can be transferred through an electrode tip to a patient's tissue.

Typical electrosurgical wave generators generate various operating frequencies of RF electrical energy and output power levels. The specific operating frequency and power output of a wave generator varies based upon the particular electrosurgical generator used and the needs of the physician during the electrosurgical procedure. The specific operating frequency and power output levels must be manually adjusted on the wave generator by a physician or other operating room personnel. Generally, wave generators used for electrosurgery are adapted to produce RF waves with an output power in the range of 1-300 W in a cut mode and 1-120 W in coagulation mode, and a frequency in the range of 300-600 kHz. Typical wave generators are adapted to maintain the selected settings during the electrosurgery.

Figure 16:
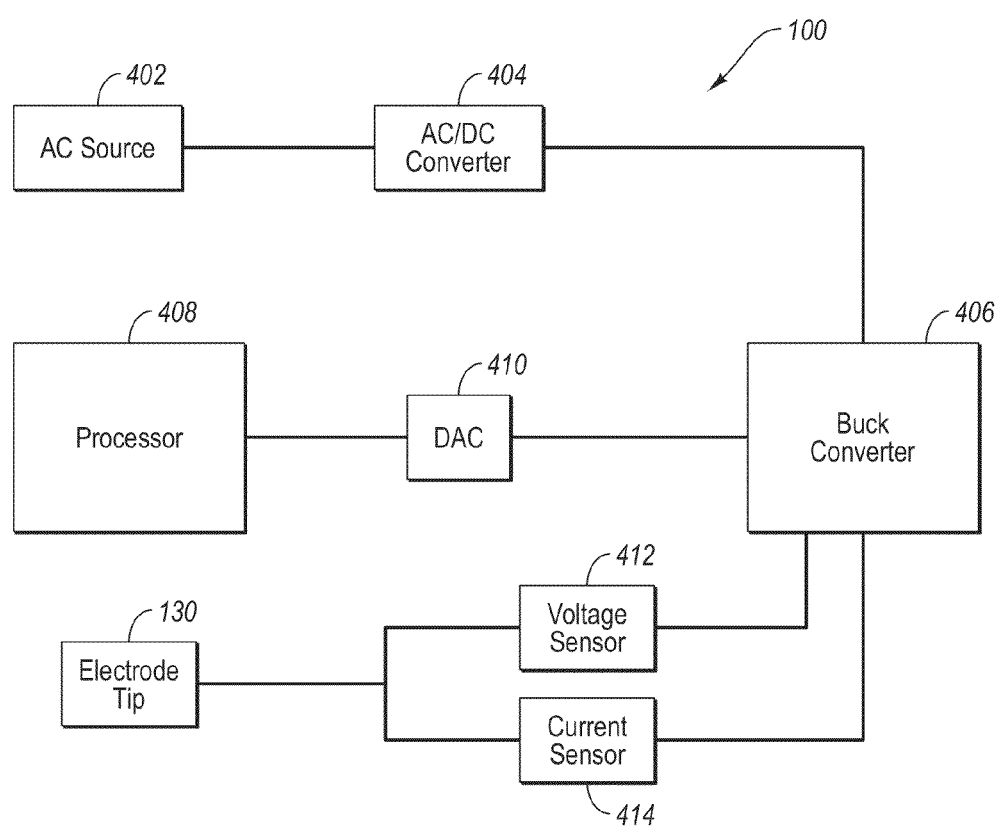
FIG. 16 is a schematic diagram illustrating components of an exemplary electrosurgical circuit according to the present invention.

FIG. 16 is a schematic representation of electrosurgical system 100 of FIG. 1. Electrosurgical system 100 is powered by an AC source 402 which provides either 120 V or 240 V. The voltage supplied by AC source 402 is directed to an AC/DC converter 404 which converts the 120 V or 240 V of alternating current to 360 V of direct current. The 360 V of direct current is then directed to a buck converter 406. Buck converter 406 is a step-down DC to DC converter. In one embodiment, buck converter 406 is adapted to step-down the incoming 360 V to a desired level within a range between 0-150 V.

Electrosurgical system 100 also includes a processor 408. Processor 408 can be programmed to regulate various aspects, functions, and parameters of electrosurgical system 100. For instance, processor 408 can determine the desired output power level at electrode tip 130 and direct buck converter 406 to step-down the voltage to a specified level so as to provide the desired output power.

Connected between processor 408 and buck converter 406 is a digital-to-analog converter ("DAC") 410. DAC 410 is adapted to convert a digital code created by processor 408 to an analog signal (current, voltage, or electric charge) which governs the voltage step-down performed by buck converter 406. Once buck converter 406 steps-down the 360 V to that level which processor 408 has determined will provide the desired output power level, the stepped-down voltage is directed to electrode tip 130 to effectuate electrosurgical cutting of a patient's tissue. Voltage sensor 412 and current sensor 414 are adapted to detect the voltage and current present in the electrosurgical circuit and communicate the detected parameters to processor 408 so that processor 408 can determined whether to adjust the output power level.

Figure 17:
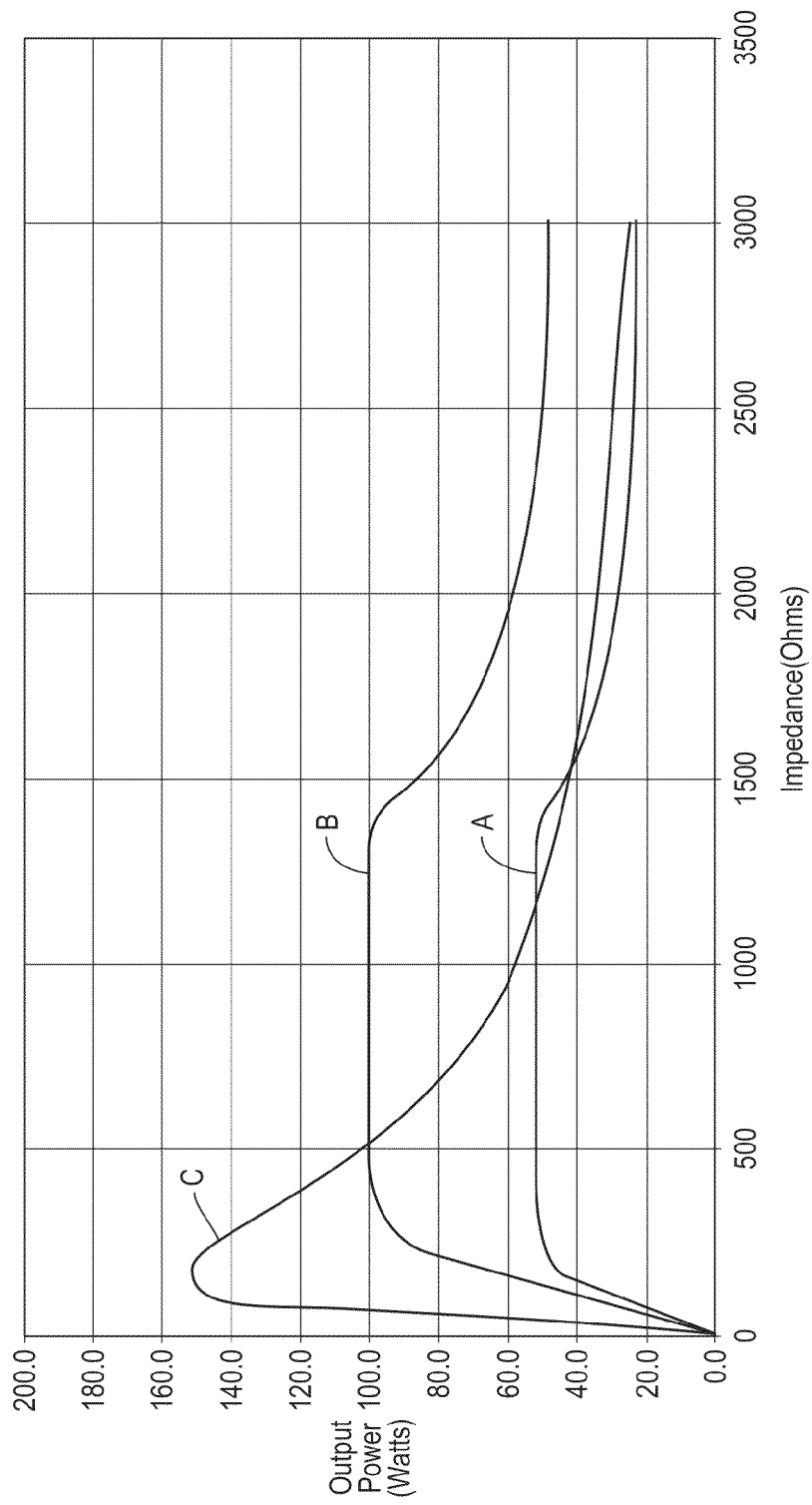
FIG. 17 is a graphical illustration of various power curves produced by electrosurgical wave generators.

As noted above, typical wave generators are adapted to maintain the selected settings throughout an electrosurgical procedure. For example, FIG. 17 illustrates power curves A and B which are representative of typical power profiles generated by wave generators known in the art. In the case of power curve A, the output power level was manually set to 50 W, while the output power level for power curve B was manually set to 100 W. Each of power curves A and B has an extended plateau portion at their respective output power level settings. These extended plateau portions graphically illustrate how typical wave generators maintain the manually selected output power level while the electrode tip is activated. With power settings in the range of 1-300 W as illustrated with power curves A and B, the wave generator must maintain the power at a constant level in order to create sufficient heat at the electrode tip to cut tissue. However, as discussed above, maintaining such power levels can cause undesirable damage to the tissue, such as necrosis and/or charring of the tissue.

In contrast, exemplary embodiments of wave generator 110 of the present invention are adapted to create a power curve such as power curve C illustrated in FIG. 17. Unlike power curves A and B, various parameters of power curve C, such as frequency and power level, are not manually set by a physician or other personnel, but are programmed into, and automatically adjusted by wave generator 110 based on parameters sensed through the electrode and fed back to wave generator 110 as described herein. Furthermore, power curve C does not necessarily maintain a particular output setting for the entire time the electrode tip is activated. Rather, processor 408 and voltage and current sensors 412 and 414 detect various parameters of the electrosurgical circuit, such as the impedance of a patient's tissue, and automatically adjust the various output parameters based on the sensed circuit parameters as described herein. Sensors used in electrosurgical circuits for detecting/measuring circuit parameters, such as voltage and current, are well known in the art. Further, any processor capable of performing the functions described herein can be used in association with wave generator 110.

In an exemplary embodiment, wave generator 110 is programmed with a specific output power curve, generally denoted as power curve C in FIG. 17. To produce the programmed power curve, voltage and current sensors 412 and 414 of wave generator 110 detect the voltage and the current of the electrosurgical circuit and forward the measurements to processor 408, which calculates the circuit/tissue impedance. Based upon the circuit/tissue impedance, processor 408 automatically adjusts the output power to that level on the programmed output power curve associated with the detected/calculated circuit/tissue impedance. Processor 408, through voltage and current sensors 412 and 414, is adapted to sample the voltage and current of the electrosurgical circuit, calculate the circuit/tissue impedance, and adjust the output power level about every 20 milliseconds. Sampling the circuit parameters and adjusting the output power every 20 milliseconds enables wave generator 110 to respond to rapid changes in the circuit/tissue impedance so as to prevent unwanted tissue damage as described here. Furthermore, as discussed above, the shaped or sharpened working edge of the electrode tip cause a larger, more quickly detectable change in the impedance without a correspondingly large temperature increase.

As can be seen on power curve C in FIG. 17, when the electrosurgical procedure is initiated, the tissue impedance is at or near 0Ω. As the RF signal is transmitted from wave generator 110, through electrode tip 130, and into the patient's tissue, the tissue impedance begins to rise. The rise of the tissue impedance from 0Ω to a predetermined impedance level is associated with a rapid increase in the output power level. The increased power level causes the electrode tip to cut through the tissue and come into contact with fresh tissue. The fresh tissue has a lower impedance level than the previously cut tissue, thereby allowing the power level to remain high, facilitating cutting of the fresh tissue. As illustrated in FIG. 17, the maximum output power level for wave generator 110 is substantially higher than that of typical wave generators known in the art.

As the tissue impedance level rises, the likelihood of tissue damage also rises. Therefore, if the tissue impedance exceeds the predetermined impedance level, the output power level rapidly falls off to below a predetermined power level to prevent undesirable tissue damage. As discussed in greater detail below, above the predetermined impedance level, wave generator 110 reduces the output power in inverse proportion to further increases in the tissue impedance above the predetermined impedance level. The output power level remains below the predetermined power level until the tissue impedance falls below the predetermined impedance level. Once the tissue impedance decreases below the predetermined impedance level, the output power level again begins to rise as described above.

In other words, wave generator 110 is programmed to create a power curve which rapidly increases the output power from 0 W to a power level substantially higher than that produced by a typical wave generator. Wave generator 110 also maintains the higher power level until the tissue impedance reaches a predetermined maximum, at which point wave generator 110 rapidly reduces the output power so as not to cause unwanted tissue damage. Once the tissue impedance falls below the predetermined maximum, wave generator 110 rapidly increases the output power level to enable cutting of the tissue. This cycle continues as long as the electrode tip is activated and in contact with patient tissue.

Figure 18:
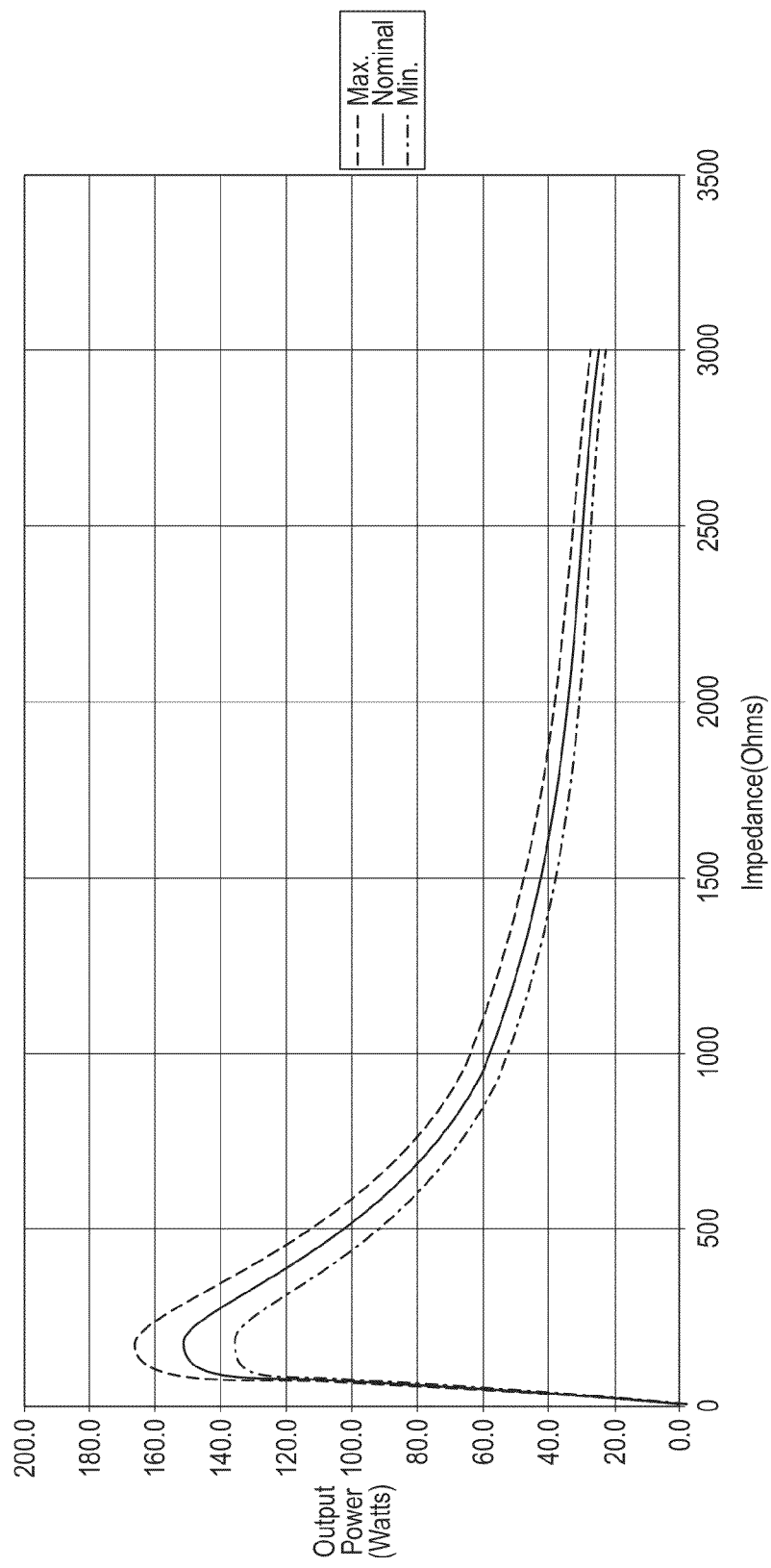
FIG. 18 is a graphical illustration of exemplary customized power curves according to the present invention.

It will be appreciated that the values illustrated in FIG. 17 for the output power levels and impedances for power curve C are for illustration purposes only. For example, the output power levels produced by a particular wave generator or for a particular procedure may be higher or lower than those illustrated in FIG. 17. To illustrate, FIG. 18 depicts multiple exemplary power curves contemplated within the scope of the present invention in which the output power levels associated with specific impedance values are higher or lower that those illustrated in FIG. 17 in relation to power curve C. In general, FIG. 18 illustrates approximate upper and lower boundaries for the presently preferred output power curve. As graphically illustrated in FIG. 18, the desirable results described herein are still obtained with the output power levels that are higher or lower than those of the presently preferred power curve C, illustrated in FIG. 17. Similarly, it will also be appreciated that the impedance values associated with a particular output power level may also be different, based on the wave generator used or a specific procedure. Finally, it will be appreciated that the power curve of the present invention may have impedance levels associated with output power levels that are different from those illustrated in FIGS. 17 and 18 or not illustrated at all in the Figures.

Following is a further discussion of how the customized power curve of the present invention reduces the amount of undesirable tissue damage around an incision site. During this discussion of the customized power curve, reference will be made to FIG. 19, which illustrates an electrode tip 500 creating an incision 502 within tissue 504 at a velocity $V_{cut}$ and at an output power P.

As described above, the change in tissue temperature $\partial T_t$ causes the electrosurgical effect, and $\lambda$ represents how deep into the tissue the electrosurgical effect is realized. The product of the tissue desiccation depth $\lambda$ and the average temperature rise $\partial T_t$ of the tissue over the depth are approximately related to the electrode tip length L, the tissue density $\rho_t$, and the tissue heat capacity $C_t$ by the following:

$$\lambda^2 \partial T_t = \frac{RLP}{2V_{cut}\rho_t C_t \rho_{c0}} \qquad \text{Equation 8}$$

Equation 8 can be inverted to solve for the power P as a function of the impedance R, resulting in:

$$P = \frac{K_0}{R}\lambda^2 \partial T_t \qquad \text{Equation 9}$$

where $$K_0 = \frac{2V_{cut}\rho_t C_t \rho_{c0}}{L} \qquad \text{Equation 10}$$

From Equation 9 it can be seen that the power P is inversely proportional to the impedance R and directly proportional to the quantity $\lambda^2 \partial T_t$. As will be understood from the disclosure herein, the quantity $\lambda^2 \partial T_t$ is related to the amount of cumulative tissue damage or potential necrosis near the electrosurgical site.

When a constant power generator is used, such as those used to generate power curves A and B of FIG. 17, the amount of tissue damage (i.e., the quantity $\lambda^2 \partial T_t$) will vary inversely to the impedance R because of changes in the contact area A and the tissue bulk resistivity $\rho_c$ (See Equation 1). In other words, the only way to maintain power P at a constant level when the impedance R increases is to increase the quantity $\lambda^2 \partial T_t$ (i.e., the amount of damage caused to the tissue).

By allowing or forcing the electrosurgical generator to reduce the output power P according to the inverse of the electrosurgical impedance R, the amount of tissue damage (i.e., $\lambda^2 \partial T_t$) can be held constant despite variations in the contact area A and tissue bulk resistivity $\rho_c$. For instance, as the impedance changes, whether due to changes in the temperature of the tissue or the amount of contact area between the electrode tip and the tissue, the power supplied to the electrode tip is automatically adjusted to account for these changes. By way of example, when the electrode tip penetrates deeper into the tissue, the contact area A between the electrode tip and the tissue increases. The increase in the contact area A reduces the impedance R between the electrode tip and the tissue (see Equation 1). The reduced impedance R, in turn, causes the power P provided by the generator to increase (see Equation 9), thereby enhancing the cutting effect and making it easier for the surgeon to make the deeper cut.

Similarly, the system compensates for varying surgical techniques, such as cutting speed. From Equations 9 and 10, it can be seen that the output power P is directly related to the cutting speed $V_{cut}$. As a surgeon moves the electrode tip through the tissue, the electrode tip comes into contact with fresh tissue as described above. The fresh tissue has a lower impedance R than the tissue that has already been cut. Therefore, as the electrode tip is moved through the tissue at a faster rate, the impedance remains relatively constant due to continuously contacting fresh tissue. The relatively constant impedance helps maintain a higher power level, resulting in an enhanced cutting effect and speed. In contrast, if the electrode tip is moved through the tissue slowly, the tissue temperature and, therefore, the impedance begins to rise. The increasing impedance causes a drop in the output power and the cutting effect. Thus, monitoring the impedance R and adjusting the output power P based upon the changing value of the impedance R as described above provides a self-limiting and self-regulating feedback mechanism which automatically compensates for variations in tissue content and surgical technique.

Figure 20:
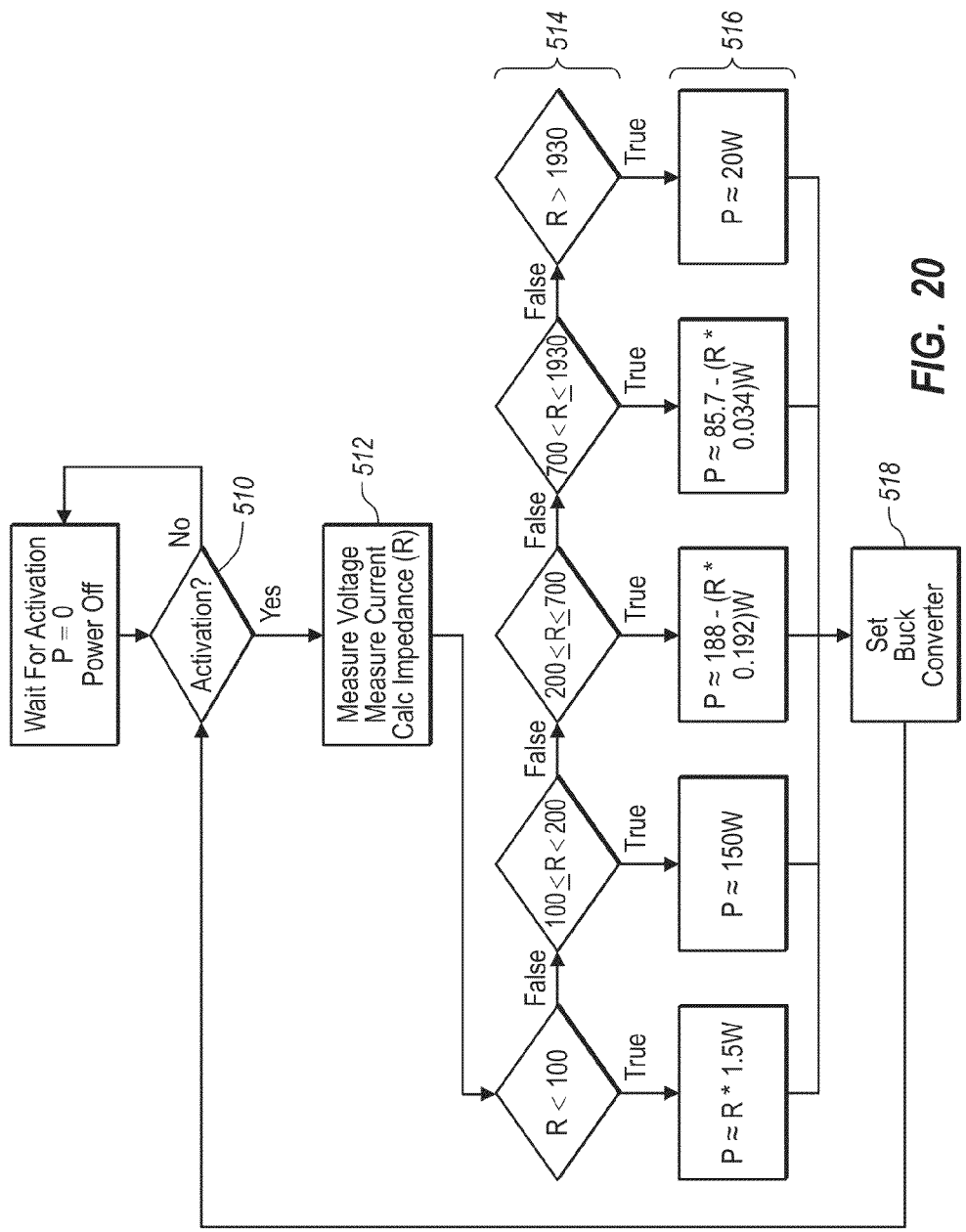
FIG. 20 illustrates a simplified electrode tip cutting through the tissue of a patient at a velocity $V_{cut}$.
Figure 21:
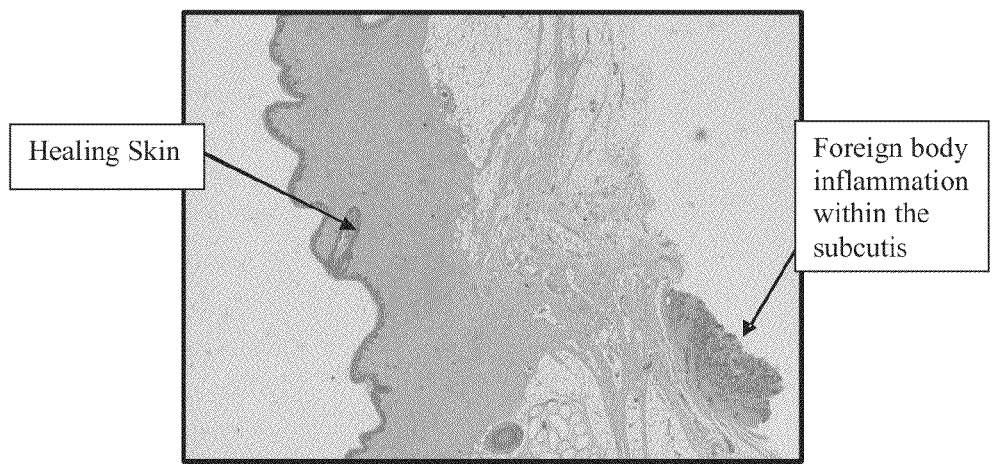
FIGS. 21-24 show the healing progress of tissue samples in which incisions were made using a surgical scalpel.
Figure 22:
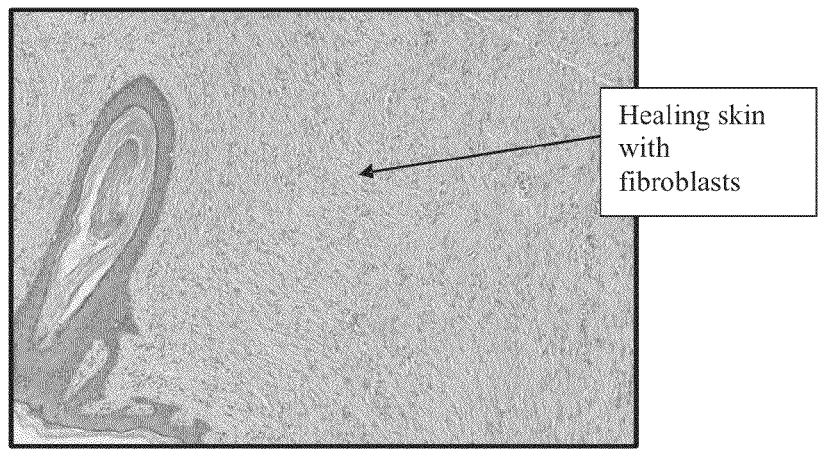

With Continued reference to FIGS. 16-18, attention is now directed to FIG. 20, which illustrates a method for approximating power curve C illustrated in FIG. 17, or any of the power curves illustrated in FIG. 18. According to the method, processor 408 determines whether electrode tip 130 has been activated in step 510. The processor will continue to monitor the activation status of electrode tip 130 until activation has been detected. Once electrode tip 130 has been activated, voltage and current sensors 412 and 414 measure various circuit parameters, such as the voltage and current, in step 512. These measurements are forwarded to processor 408, which in turn calculates the circuit/tissue impedance. The circuit/tissue impedance can be calculated by comparing the voltage supplied by the wave generator 110 to the current flowing through the circuit, for example.

Once processor 408 has determined the circuit/tissue impedance, processor 408 then compares the circuit/tissue impedance to various predetermined impedance ranges and classifies the circuit/tissue impedance within one of those ranges in step 514. For example, as illustrated in FIG. 20, the calculated impedance value is compared to and classified within one of five impedance ranges, namely impedances approximately less than 100Ω, between 100-199Ω, between 200-700Ω, between 701-1930Ω, and over 1930Ω.

With the calculated impedance classified within the correct range, processor 408 calculates the appropriate output power to be provided through electrode tip 130 in step 516. For example, if the calculated impedance is less than 100Ω, processor 408 calculates the appropriate output power level by multiplying the calculated impedance by about 1.5. If the calculated impedance is greater than or equal to 100Ω and less than 200Ω, processor 408 sets the output power level to approximately 150 watts. If the calculated impedance is greater than or equal to 200Ω and less than or equal to 700Ω, processor 408 calculates the appropriate output power level by multiplying the calculated impedance by about 0.192 and subtracting that value from about 188. Similarly, for impedances greater than 700Ω and less than or equal to 1930Ω, processor 408 calculates the appropriate output power level by multiplying the calculated impedance by about 0.034 and subtracting that value from about 85.7. Finally, for calculated impedances above 1930Ω, the output power is set at approximately 20 W.

It will be appreciated that the various calculated impedance ranges shown in FIG. 20 and described above are exemplary only. Similarly, the calculations used to determine the appropriate output power level for each of the impedance ranges as illustrated in FIG. 20 and described above are also for illustration only and are not intended to limit that scope of the present invention. Further, as alluded to above, the desirable results described herein are obtained even when the output power curve varies above or below the exemplary values set forth above. The specific values for the output power are, as described above, inversely proportional to the tissue impedance detected by the electrode tip.

Once processor 408 has calculated the appropriate output power level for the calculated impedance of the circuit, processor 408 directs buck converter 406 to adjust the output power level to match the desired output power level calculated above in step 518. Processor 408 then returns to the initial step of detecting whether electrode tip 130 is still activated. If processor 408 determines that electrode tip 130 is no longer activated, then the power through electrode tip 130 is turned off and processor 408 continues to monitor the activation status of electrode tip 130. If processor 408 determines that electrode tip 130 is still activated or has been reactivated, then wave generator 110 again determines the circuit/tissue impedance and adjusts the output power level as described above.

Wave generator 110 can thus be adapted to sense the circuit parameters, calculate the tissue impedance, and adjust the output power P in response to the changing tissue impedance. Additionally, generator 110 can perform this self-limiting process substantially in real-time (i.e., a 20 millisecond cycle). This is significant because, as noted above, the likelihood of tissue damage increases as tissue impedance increases. Therefore, adjusting the output power level substantially in real-time relative to changes in tissue impedance enables wave generator 110 to reduce or eliminate incidences of unwanted tissue damage.

Clinical Trial Examples

Clinical trials were conducted to compare the speed and quality of healing of incisions created by different devices. In the trials, six incisions were made in porcine skin using different devices. In particular, two incisions were made with each of i) a surgical scalpel; ii) a standard electrosurgical system using a coated, non-sharpened blade (MegaDyne catalog no. 0012, 0.33 mm) at 50 W, referred to herein as standard cautery system; and iii) an electrosurgical system according to an exemplary embodiment of the present invention, namely, a system using an electrode with a sharpened edge and a wave generator programmed with a customized power curve as described herein, referred to herein as a prototype cautery system. The incisions were sutured closed and monitored for 30 days. After two weeks the sutures were removed, and after 30 days the incisions sites were harvested and analyzed. Each of the incisions was divided into three sections for analysis.

The first two incisions, shown in FIGS. 21-24, were made with a standard surgical scalpel. Analysis of the first scalpel incision, shown in FIGS. 21 and 22 below, revealed the following:

Skin section 1: This skin section did not have any microscopic changes.

Skin section 2: Focally within the subcutaneous tissue of this skin section was a partial piece of suture material surrounded and infiltrated by a mild to moderate amount of foreign body inflammation and fibrosis. Focally in the superficial to deep dermis overlying the suture material the dermal tissue had a mild increase in fibrous connective tissue and with small numbers of fibroblasts admixed with the dermal collagen fibers. The epidermis covering the skin sections was normal.

Skin section 3: This skin section had an artery within the subcutis that was partially obstructed with an organized tissue attached to the intimal layer of the vessel. This organized tissue could be intimal proliferation or an organized thrombus.

Figure 23:
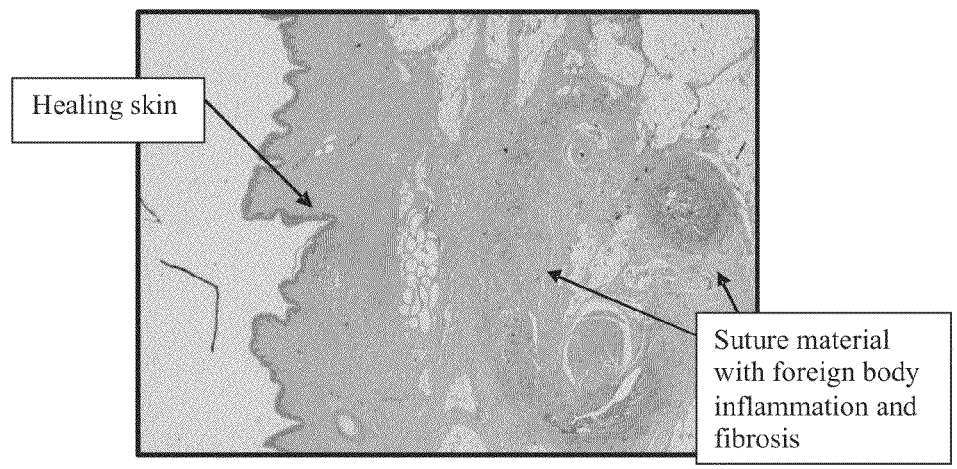
Figure 24:
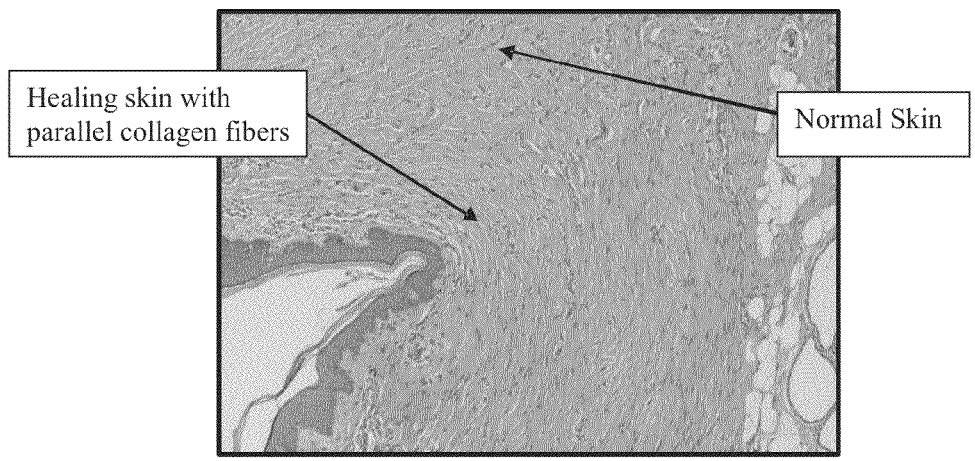
Figure 25:
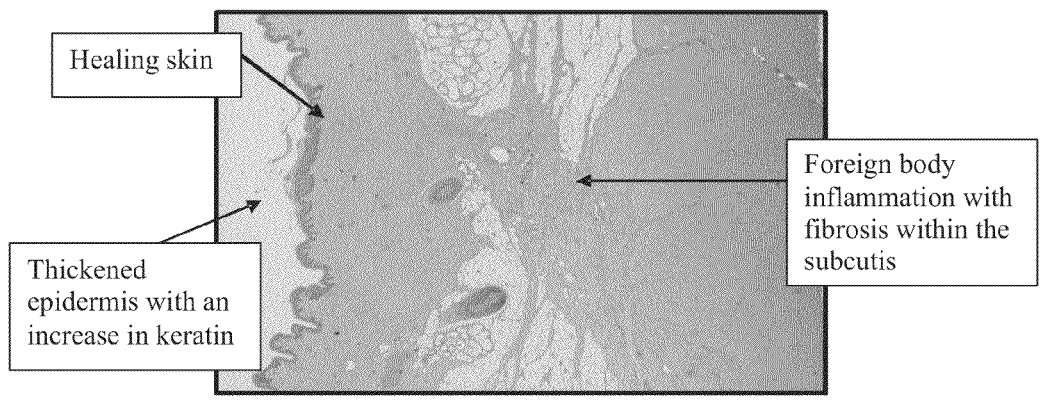
FIGS. 25-28 show the healing progress of tissue samples in which incisions were made using a standard electrosurgical system with a coated, non-sharpened blade.
Figure 26:
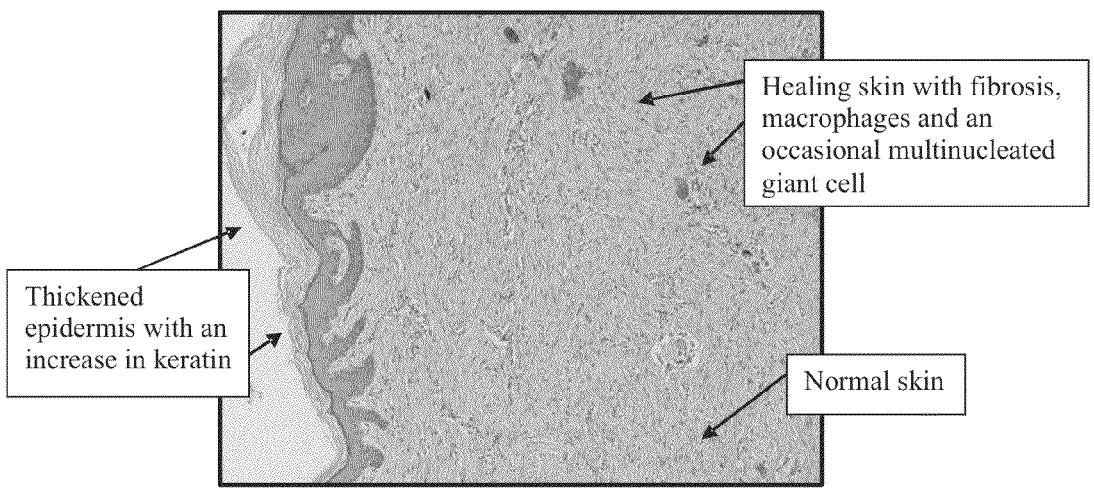

Similarly, analysis of the three sections of the second scalpel incision, shown in FIGS. 23 and 24, revealed the following:

Skin section 1: There was a small focus of organized parallel connective tissue/collagen fibers in the superficial to deep dermis of this tissue section. The epidermis was normal. Also within this skin section, somewhat below the dermal fibrosis, there was a long thin focus of fibrous connective tissue transversing the muscle layer below the subcutis. Within the area immediately adjacent to the connective tissue were several degenerating and regenerating myofibers.

Skin section 2: There was a small focus of organized parallel connective tissue/collagen fibers in the superficial to deep dermis of this tissue section. The epidermis was normal. Subjacent to the dermal fibrosis, in the subcutis tissue, were two large sections of clear suture material surrounded and infiltrated by a large amount of foreign body inflammation and fibrosis. There was a small thin focus of fibrous connective tissue accompanied by a few regenerating myofibers transversing the muscle layer below the subcutis, adjacent to where the suture material is. There were small areas of hemorrhage within the granulomatous inflammation surrounding the suture material and on the deep edge of the skin section. The hemorrhage is likely from histology processing of the tissues.

Skin section 3: There was a small focus of organized parallel and wavy connective tissue/collagen fibers in the superficial to deep dermis of this tissue section. The epidermis was normal.

The next two incisions, shown in FIGS. 25-28, were made with a standard cautery system using. Analysis of the three sections of the first standard cautery incision, shown in FIGS. 25 and 26, revealed the following:

Skin section 1: Focally within the dermis was a moderate amount of maturing fibrous connective tissue containing several small vessels and a few multinucleated giant cells and macrophages. The epidermis overlying this area of dermis was minimally hyperplastic with a mild increase in keratin. The fibrous connective tissue of the dermis extended from the deep dermis, through the subcutis tissue and into the muscle layer below the subcutis. Admixed throughout the connective tissue of the subcutis and muscle layer were individual to small nests of multinucleated giant cells, macrophages (some containing melanin), and lymphocytes (foreign body inflammation).

Skin section 2: Focally within the dermis was a moderate amount of maturing fibrous connective tissue containing several small vessels and a few multinucleated giant cells and macrophages. The epidermis overlying this area of dermis was minimally hyperplastic with a minimal increase in keratin. The surface of the skin within the area of the dermal fibrosis was mildly bulging. The dermal connective tissue extended from the deep dermis into the superficial subcutis. Accompanying the connective tissue in the subcutis was a mild amount of foreign body inflammation.

Skin section 3: Focally within the dermis was a moderate amount of maturing fibrous connective tissue containing several small vessels and a few multinucleated giant cells and macrophages. The epidermis overlying this area of dermis was minimally hyperplastic with a minimal increase in keratin. The surface of the skin within the area of the dermal fibrosis was mildly bulging. Within the subcutis, just below the area of dermal fibrosis, was a large section of clear suture material surrounded by mature fibrous connective tissue admixed with a foreign body inflammation. The tissue reaction surrounding the suture material extended into the muscle layer, below the subcutis.

Figure 27:
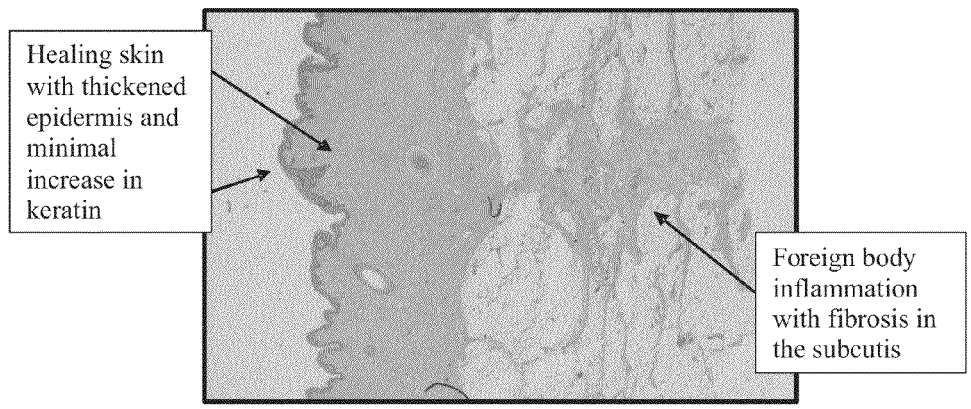
Figure 28:
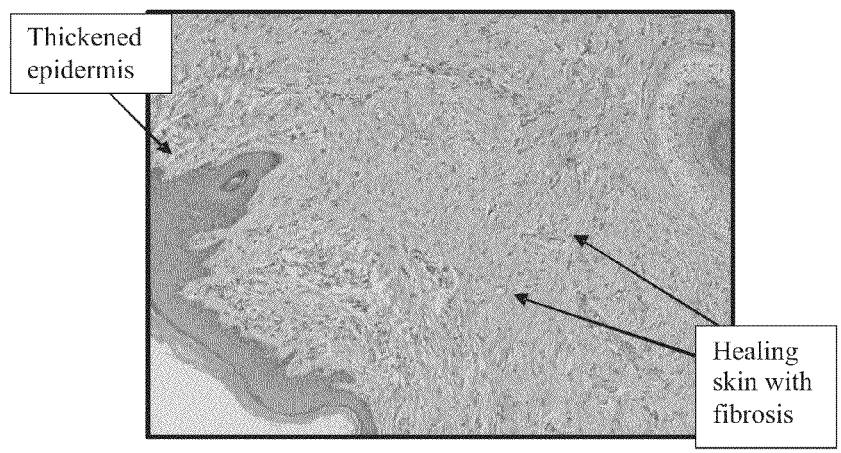
Figure 29:
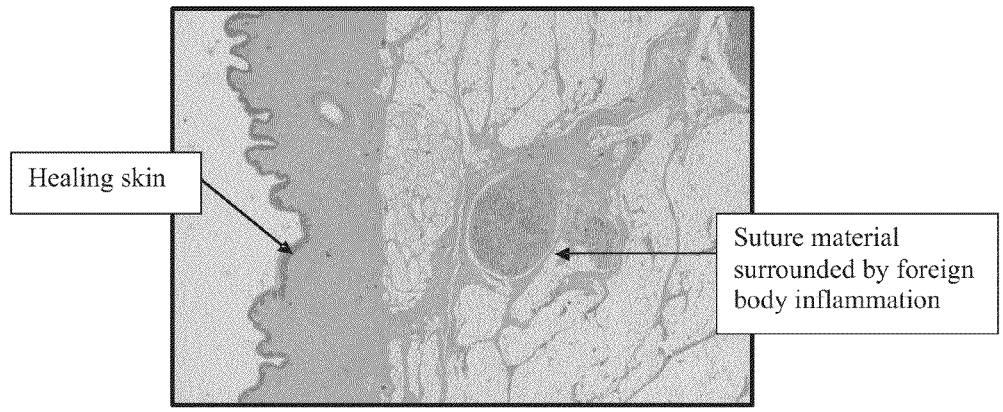
FIGS. 29-32 show the healing progress of tissue samples in which incisions were made using an electrosurgical system with a sharpened electrode and a customized power curve according to an exemplary embodiment of the present invention.
Figure 30:
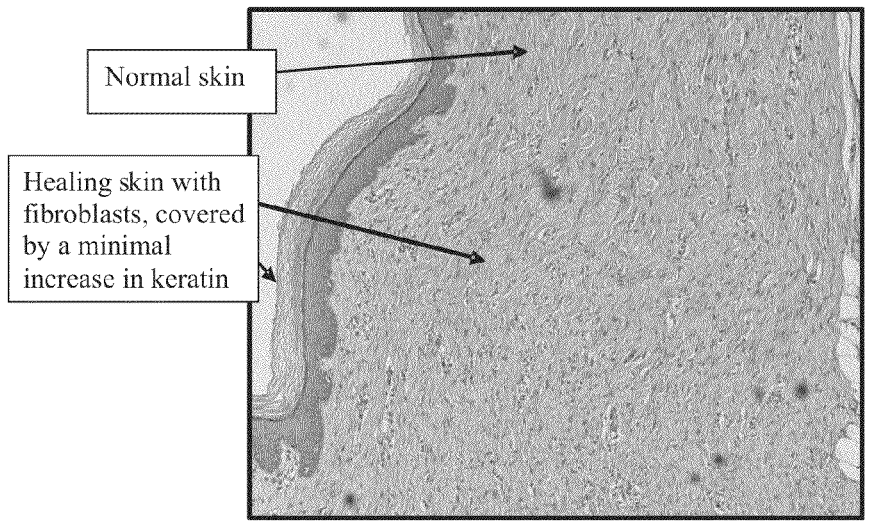

Similarly, analysis of the three sections of the second standard cautery incision, shown in FIGS. 27 and 28, revealed the following:

Skin section 1: Focally within the dermis was a mild amount of maturing fibrous connective tissue containing several small vessels. The epidermis overlying this area of dermis was minimally hyperplastic with a minimal increase in keratin. Within the subcutis, just below the area of dermal fibrosis, was a large section of clear suture material surrounded by mature fibrous connective tissue admixed with a foreign body inflammation.

Skin section 2: Focally within the dermis was a mild amount of maturing fibrous connective tissue containing several small vessels. The epidermis overlying this area of dermis had a minimal increase in keratin. The connective tissue of the dermis mildly infiltrated the subjacent subcutis, and there were small numbers of multinucleated giant cells within the subcutis admixed with the connective tissue and adjacent to. The muscle layer below the subcutis fibrosis contained a small focus of foreign body inflammation. There was a small amount of hemorrhage on the edge of the tissue section, which is secondary to histology processing of the tissues.

Skin section 3: Focally within the dermis was a mild amount of maturing fibrous connective tissue containing several small vessels. The epidermis overlying this area of dermis was minimally hyperplastic with a minimal increase in keratin. The fibrosis of the dermis extended focally into the deep subcutis. Within the subcutis connective tissue were several small vessels accompanied by very few macrophages and an occasional multinucleated giant cell. There was a small amount of hemorrhage on the edge of the tissue section, which is secondary to histology processing of the tissues.

Finally, the two incisions shown in FIGS. 29-32 were made with a prototype cautery system using a sharpened electrode in combination with customized power curve according to an example embodiment of the present invention. Analysis of the three sections of the first prototype cautery incision, shown in FIGS. 29 and 30, revealed the following:

Skin section 1: Focally within the dermis there was a minimal increase in fibroblasts admixed with the collagen fibers. The epidermis overlying this area of dermis was minimally hyperplastic. The dermal fibrosis minimally extended into the subcutis. There were a few multinucleated giant cells within the connective tissue of the subcutis (foreign body inflammation). There was a small focus of fibrosis within the muscle layer. There were three areas of foreign body inflammation within the superficial to deep dermis to superficial subcutis tissue. The inflammation within the superficial dermis was infiltrating the adjacent epidermis and there was a small area of epidermal degeneration.

Skin section 2: Focally within the dermis there was a minimal increase in fibroblasts admixed with the collagen fibers. The epidermis overlying this area of dermis was minimally hyperkeratotic. The dermal fibrosis extended into the subjacent subcutis tissue. The subcutaneous connective tissue was surrounding a large section of clear suture material. There was also a foreign body inflammation admixed in the subcutaneous connective tissue. There was a moderate focus of fibrosis within the muscle layer below the subcutis fibrosis and inflammation.

Skin section 3: Focally within the dermis there was a minimal increase in fibroblasts admixed with the collagen fibers. The epidermis overlying this area of dermis was normal. There was a moderate focus of fibrosis within the muscle layer near where the dermal fibrosis was.

Figure 31:
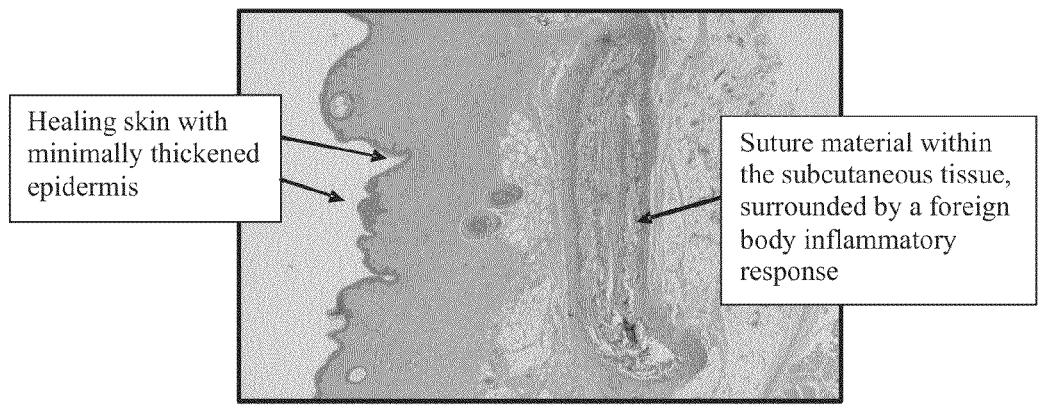
Figure 32:
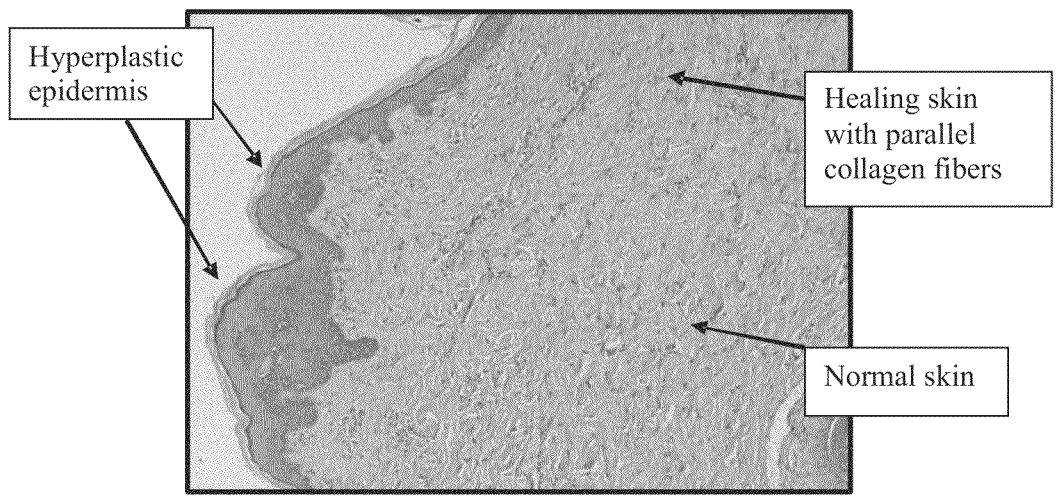

Similarly, analysis of the three sections of the second prototype cautery incision, shown in FIGS. 31-32, revealed the following:

Skin section 1: Focally within the dermis was a scant increase in fibroblasts with more organization of the collagen fibers than the surrounding dermis. The epidermis was normal. There were two small pieces of clear suture material admixed with a few macrophages and multinucleated giant cells within the superficial subcutis, just below the area of dermis mentioned above. There was a large focus of fibrosis within the deep subcutis and subjacent muscle layer.

Skin section 2: There were no microscopic changes in this tissue section.

Skin section 3: Focally within the dermis was a scant increase in fibroblasts with more organization of the collagen fibers than the surrounding dermis. The epidermis was normal. There was a large segment of clear suture material surrounded and infiltrated by mature fibrous connective tissue and a foreign body inflammation within the subcutis, below the area of dermis mentioned above. There was a moderate focus of fibrosis in the muscle tissue subjacent to the subcutaneous suture material.

Although there was what would be considered normal healing of the epidermis, dermis, subcutis and muscle layer of the skin in all of the analyzed incisions, the scalpel and prototype cautery incisions were healing faster than the incisions created by the standard cautery. For each of the incisions, there was a minimal amount of focal tissue healing left within the skin incision sites, and most of the tissue healing was found mainly in the dermis. Additionally, there was a minimal amount of fibroblasts with parallel orientation of the dermal collagen fibers in the scalpel and prototype cautery incision sites. However, the standard cautery incision sites contained more fibroblasts and connective tissue still within the dermal healing incision sites than found in the scalpel and prototype cautery healing skin incisions. Also, there was epidermal hyperplasia and/or hyperkeratination in all of the standard cautery healing incision sites, whereas only two of the prototype cautery healing skin incision sites had minimal epidermal hyperplasia and/or hyperkeratination, and none of the scalpel healing skin sites had any epidermal changes. Epidermal hyperplasia and hyperkeratination are results of chronic irritation. Therefore, it will be readily apparent to one of ordinary skill in the art that the prototype cautery of the present invention produces results which are similar to the results produced by a typical surgical scalpel and which are much improved over the results of a standard cautery system.

Thus, as discussed herein, the embodiments of the present invention embrace the utilization of a sharpened, limited mass/thickness electrode tip in combination with a customized power curve. The electrode tip can be sharpened in order to concentrate the electrical energy at the point of incision. The mass/thickness of the electrode tip can be limited to prevent buildup of latent heat that can cause undesirable tissue damage. The power curve is characterized by a maximum output power level that is substantially higher than that typically used in electrosurgery, and which is automatically adjusted in real-time based on the circuit/tissue impedance. The output power of the customized power curve can be automatically adjusted so that it remains inversely proportional to the circuit/tissue impedance. Combining the use of the sharpened, limited mass/thickness electrode tip with the customized power curve reduces or eliminates unwanted tissue damage at and around the incision point. Reduction in tissue damage reduces incidences of post-operative complications and increases the quality and speed of post-operative recovery and healing.

While the methods and processes of the present invention have proven to be particularly useful in the area of electrosurgery, those skilled in the art can appreciate that the methods and processes of the present invention can be used on a variety of different kinds of surfaces and in a variety of different areas of application for performing a particular task.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical system comprising:
    an electrosurgical electrode adapted to transmit electrical energy to patient tissue during an electrosurgical procedure, the electrode having a configuration that enhances rapid feedback used to automatically correct and regulate power levels applied to the electrode, the electrode comprising a working surface that is sharpened to concentrate the electrical energy transmitted from the electrode to the patient tissue during an electrosurgical procedure so that concentration of the electrical energy to the patient tissue improves both speed with which the electrode is able to cut or cauterize the tissue while also reducing likelihood of tissue damage in tissue surrounding the cut or cauterized tissue, the improved speed with which the electrode is able to cut or cauterize tissue providing more rapid feedback that can be used to regulate power levels applied to the electrode; and
    an electrosurgical wave generator electrically coupled to the electrode, the wave generator comprising;
        a power source for providing electrical energy to said electrode working surface at a specified frequency;
        at least one of a voltage sensor and a current sensor coupled between the power source and the electrode for sensing one or more electrical feedback parameters from which the tissue impedance can be essentially continuously sampled so that the tissue impedance can be used to rapidly adjust power levels applied to the electrode during a cut or cauterize procedure to avoid application of excess power and tissue damage; and a processor programmed with executable instructions for processing the sensed electrical parameters to re-compute tissue impedance for each sample taken while cutting or cauterizing the tissue so that (i) as cutting or cauterizing the tissue is initiated, power to the electrode is rapidly increased up to a pre-determined tissue impedance level, and then (ii) as tissue impedance increases above the pre-determined tissue impedance level, the power to the electrode is rapidly reduced in inverse proportion to further increases in tissue impedance.

2. An electrosurgical system as recited in claim 1, wherein the sharpened working surface of the electrode has a thickness of between about 0.0254 mm and about 0.127 mm.

3. An electrosurgical system as recited in claim 1, wherein the electrode has a reduced mass to minimize the amount of latent heat retained by the electrode and transferred to the surrounding tissue.

4. An electrosurgical system as recited in claim 1, wherein the wave generator includes both a voltage and a current sensor that sense both a voltage and a current from the power applied to the electrode working surface.

5. An electrosurgical system as recited in claim 4, wherein the processor of the wave generator is programmed to calculate an impedance of the electrosurgical system from the sensed voltage and current.

6. An electrosurgical system as recited in claim 1, wherein the electrical energy level of the power applied to the electrode working surface as a result of the sampled parameters and the re-computed tissue impedance for each sample corresponds to a customized power curve that is inversely proportional to the impedance of the tissue once the impedance reaches the pre-determined tissue impedance level as determined during the cut or cauterize procedure based on the samples.

7. An electrosurgical system as recited in claim 6, wherein the wave generator comprises a processor that is programmed to:
use the computed impedance of each sample to calculate the electrical energy level on the customized power curve associated with the computed impedance level; and
adjust the level of electrical energy being transmitted through the electrode working surface to the level on the customized power curve associated with the computed impedance.

8. An electrosurgical system as recited in claim 7, wherein, prior to determining that the tissue impedance has reached the pre-determined tissue impedance level, the customized power curve maintains the electrical energy being transmitted to the patient tissue at a maximum power level, which corresponds to tissue impedance levels on the customized power curve of between about 100 ohms and about 200 ohms.

9. An electrosurgical system as recited in claim 8, wherein the maximum power level of electrical energy transmitted to the patient tissue is about 150 watts.

10. An electrosurgical system as recited in claim 1, wherein the electrical parameters are sampled and the tissue impedance is re-computed so that the wave generator is capable of adjusting the level of a lied power at the electrode working surface about every 20 milliseconds.

11. An electrosurgical system comprising:
an electrosurgical electrode adapted to transmit electrical energy to patient tissue during an electrosurgical procedure, the electrode having a configuration that enhances rapid feedback used to automatically correct and regulate power levels applied to the electrode, the electrode comprising a working edge that is sharpened to concentrate the electrical energy transmitted from the electrode to the patient tissue during an electrosurgical procedure so that concentration of the electrical energy to the patient tissue improves both speed with which the electrode is able to cut or cauterize the tissue while also reducing likelihood of tissue damage in tissue surrounding the cut or cauterized tissue, the improved speed with which the electrode is able to cut or cauterize tissue providing more rapid feedback that can be used to regulate power levels applied to the electrode, and the electrode having a limited mass which limits the amount of latent heat the electrode is able to retain; and
an electrosurgical wave generator electrically coupled to the electrode, the wave generator comprising;
a power source for providing electrical energy to said electrode working edge at a specified frequency;
a voltage sensor and a current sensor coupled between the power source and the electrode for sensing both voltage and current at the electrode at a sampling rate of about every 20 milliseconds in order to provide voltage and current feedback parameters from which the tissue impedance can be essentially continuously re-computed about every 20 milliseconds and then used to rapidly adjust power levels applied to the electrode during a cut or cauterize procedure to avoid application of excess power and tissue damage; and
a processor programmed with executable instructions for processing the sensed voltage and current to re-compute tissue impedance for each sample taken while cutting or cauterizing the tissue so that (i) as cutting or cauterizing the tissue is initiated, power to the electrode is initially rapidly increased up to a pre-determined tissue impedance level, and then (ii) as tissue impedance increases above the pre-determined tissue impedance level, the power to the electrode is rapidly reduced in inverse proportion to further increases in tissue impedance.

12. An electrosurgical system as recited in claim 11, wherein the sharpened working edge of the electrode has a thickness in the range of about 0.1270 mm to about 0.0254 mm.

13. An electrosurgical system as recited in claim 11, wherein the sharpened working edge of the electrode is coated with a non-stick coating.

14. An electrosurgical system as recited in claim 11, wherein the parameters of the electrode's working edge are used by the processor to automatically adjust the electrical energy being applied by the working edge to the patient tissue in real-time based on a sampling rate of about 20 milliseconds.

15. An electrosurgical system as recited in claim 11, wherein the wave generator is adapted to generate electrical energy in a range from about 0 watts to about 150 watts.

16. An electrosurgical system comprising:
an electrosurgical electrode adapted to transmit electrical energy to patient tissue during an electrosurgical procedure, the electrode having a configuration that enhances rapid feedback used to automatically correct and regulate power levels applied to the electrode, the electrode comprising a plurality of working surfaces with differing lengths that are angled relative to one another, but wherein each working surface has a thickness in the range of about 0.254 mm to about 0.1270 mm that is sharpened to concentrate the electrical energy transmitted from the electrode to the patient tissue during an electrosurgical procedure so that concentration of the electrical energy to the patient tissue improves both speed with which the electrode is able to cut or cauterize the tissue while also reducing likelihood of tissue damage in tissue surrounding the cut or cauterized tissue, the improved speed with which the electrode is able to cut or cauterize tissue providing more rapid feedback that can be used to regulate power levels applied to the electrode, and the electrode having an overall thickness of about 0.4318 mm so that the electrode has a limited mass which limits the amount of latent heat the electrode is able to retain; and an electrosurgical wave generator electrically coupled to the electrode, the wave generator comprising;

a power source for providing electrical energy to said electrode working surface at a specified frequency;

a voltage sensor and a current sensor coupled between the power source and the electrode for sensing both voltage and current at the electrode at a sampling rate of about every 20 milliseconds in order to provide voltage and current feedback parameters from which the tissue impedance can be essentially continuously re-computed about every 20 milliseconds and then used to rapidly adjust power levels applied to the electrode during a cut or cauterize procedure to avoid application of excess power and tissue damage; and a processor programmed with executable instructions for processing the sensed voltage and current to re-compute tissue impedance for each sample taken while cutting or cauterizing the tissue so that (i) as cutting or cauterizing the tissue is initiated, power to the electrode is initially rapidly increased up to a pre-determined tissue impedance level, and then (ii) as tissue impedance increases above the pre-determined tissue impedance level, the power to the electrode is rapidly reduced in inverse proportion to further increases in tissue impedance.

17. An electrosurgical system as recited in claim 16, wherein the re-computed impedance is directly proportional to the velocity at which the electrode working edge is moved through the tissue so that the level of electrical power applied to the electrode is related to the speed at which the tissue is cut by the working edge.

18. An electrosurgical system as recited in claim 16, wherein the wave generator is adapted to generate electrical energy for transmission to patient tissue through the electrode in a range from about 0 watts to about 150 watts.

19. A computer-implemented method of controlling power to a working surface of an electrode of an electrosurgical system used to cut or cauterize a patient's tissue during a medical procedure, comprising:

providing electrical energy to said electrode working surface at a specified frequency;

sampling at a rate of about 20 milliseconds the voltage and current at said electrode working surface so that tissue impedance can be derived from the voltage and current samples and then used to rapidly adjust power levels applied to the electrode during a cut or cauterize procedure to avoid application of excess power and tissue damage; and using a processor programmed with executable instructions to process the sensed voltage and current parameters in order to re-compute tissue impedance for each sample taken while cutting or cauterizing the tissue so that (i) as cutting or cauterizing the tissue is initiated, power to the electrode is rapidly increased up to a pre-determined tissue impedance level, and then (ii) as tissue impedance increases above the pre-determined tissue impedance level, the power to the electrode is rapidly reduced in inverse proportion to further increases in tissue impedance.

20. An electrosurgical wave generator having a processor for implementing a computer-implemented method of controlling power to a working surface of an electrode of an electrosurgical system used to cut or cauterize a patient's tissue during a medical procedure, and wherein the processor includes computer-executable instructions for implementing a method comprised of:

providing electrical energy to said electrode working surface at a specified frequency;

sampling at a rate of about 20 milliseconds the voltage and current at said electrode working surface so that tissue impedance can be derived from the voltage and current samples and then used to rapidly adjust power levels applied to the electrode during a cut or cauterize procedure to avoid application of excess power and tissue damage; and using a processor programmed with executable instructions to process the sensed voltage and current parameters in order to re-compute tissue impedance for each sample taken while cutting or cauterizing the tissue so that (i) as cutting or cauterizing the tissue is initiated, power to the electrode is rapidly increased up to a pre-determined tissue impedance level, and then (ii) as tissue impedance increases above the pre-determined tissue impedance level, the power to the electrode is rapidly reduced in inverse proportion to further increases in tissue impedance.

* * * * *

UNITED STATES PATENT AND TRADEMARK OFFICE
CERTIFICATE OF CORRECTION

Page 1 of 2

PATENT NO. : 8,500,727 B2
APPLICATION NO. : 12/464591
DATED : August 6, 2013
INVENTOR(S) : Aramayo It is certified that error appears in the above-identified patent and that said Letters Patent is hereby corrected as shown below:

In the Specification

Column 4
Line 3, change "high speed monitoring" to --high-speed monitoring--
Line 6, change "efficiency, dramatic reduction" to --efficiency, a dramatic reduction--
Line 47, change "FIG. 3A" to --FIG. 3--

Figure 19:
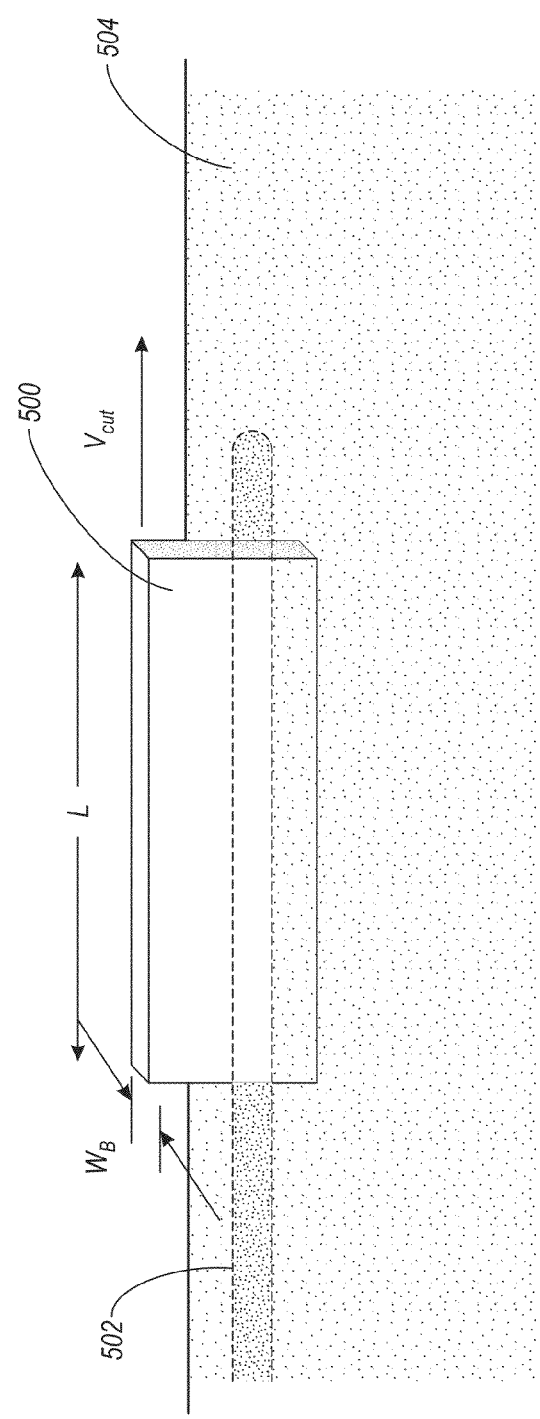
FIG. 19 is a flow diagram illustrating process steps followed by a wave generator to produce a power curve according to the present invention.

Column 5
Line 11, change "implement having sharpened edge" to --implement having a sharpened edge--
Line 14, change "of electric field" to --of an electric field--
Line 16, change "illustrates an sharpened electrode tip" to --illustrates a sharpened electrode tip--
Lines 26-28, change "FIG. 19 is a flow diagram illustrating process steps followed by a wave generator to produce a power curve according to the present invention;" to --FIG. 19 illustrates a simplified electrode tip cutting through the tissue of a patient at a velocity $V_{cut}$;--
Lines 29-30, change "FIG. 20 illustrates a simplified electrode tip cutting through the tissue of a patient at a velocity $V_{cut}$;" to --FIG. 20 is a flow diagram illustrating process steps followed by a wave generator to produce a power curve according to the present invention;--

Column 6
Line 21, change "Wave Generator" to --Wave generator--

Column 7
Line 11, change "potion" to --portion--
Line 24, change "chemical vapor deposited" to --chemical-vapor deposited--

Column 8
Line 29, change "cross sectional geometry" to --cross-sectional geometry--
Line 32, change "cross sectional shape" to --cross-sectional shape--
Line 37, change "electrode tip 220" to --electrosurgical electrode tip 210--

Signed and Sealed this
Twenty-fifth Day of March, 2014

Michelle K. Lee
*Deputy Director of the United States Patent and Trademark Office*

Column 9
Line 5, change "or focuses" to --or focus--

Column 10
Line 37, change "not illustrated has having" to --not illustrated as having--
Line 63, change "theses shaped" to --these shaped--
Line 64, change "working edge" to --working edges--

Column 11
Line 36, change "for typical" to --for a typical--
Line 42, change "of electric field" to --of an electric field--

Column 14
Line 45, change "50-100 C." to --50-100° C.--
Line 46, change "250-350 C." to --250-350° C.--

Column 15
Line 24, change "may me applied" to --may be applied--

Column 19
Line 27, change "With Continued reference" to --With continued reference--

Column 21
Line 32, change "small thin focus" to --small, thin focus--
Line 46, change "cautery system using." to --cautery system.--

Column 22
Line 55, change "with customized power curve" to --with a customized power curve--

Column 25
Line 60, change "of a lied power" to --of applied power--